United States Patent [19]

Hood et al.

[11] Patent Number: 5,382,251

[45] Date of Patent: Jan. 17, 1995

[54] PLUG PULLING METHOD

[75] Inventors: Larry L. Hood, Laguna Hills; Gregg Hughes, Lake Forest; Ted Carlson, Mission Viejo, all of Calif.; John Berkman, Grants Pass, Oreg.; James T. Caillouette, Newport Beach, Calif.; Robert C. Klapper, Los Angeles, Calif.; Woodrow W. Watson, Mission Viejo, Calif.

[73] Assignee: Biomet, Inc., Warsaw, Ind.

[21] Appl. No.: 836,109

[22] Filed: Feb. 14, 1992

Related U.S. Application Data

[63] Continuation-in-part of Ser. No. 713,959, Jun. 11, 1991, which is a continuation-in-part of Ser. No. 665,418, Mar. 5, 1991, which is a continuation-in-part of Ser. No. 304,820, Jan. 31, 1989, Pat. No. 5,019,083.

[51] Int. Cl.⁶ ............................................. A61B 17/56
[52] U.S. Cl. ........................................ 606/99; 606/86; 606/2; 623/16
[58] Field of Search ............... 128/24 A, 399, 400; 606/86, 82, 99, 92–95, 127, 128, 79, 80, 2, 15, 28; 623/22, 23, 16

[56] References Cited

U.S. PATENT DOCUMENTS

| | | |
|---|---|---|
| 33,530 | 10/1961 | Leisen . |
| 165,403 | 7/1975 | Blatt . |
| 446,078 | 2/1991 | Rouse . |
| 804,831 | 11/1905 | Cunnius . |
| 1,096,763 | 5/1914 | Smith . |
| 1,390,904 | 9/1921 | Hazelton . |
| 1,451,970 | 4/1923 | Taylor . |
| 1,483,164 | 2/1924 | Driggs . |
| 1,967,145 | 7/1934 | Fisher . |
| 2,138,245 | 11/1938 | Smith . |
| 2,257,327 | 4/1941 | Bradford . |
| 2,517,364 | 8/1950 | Torresen . |
| 2,714,890 | 8/1955 | Vang . |
| 2,784,637 | 3/1957 | Smisko . |
| 2,828,662 | 4/1958 | Antal . |
| 2,840,404 | 6/1958 | Weber, Jr. . |
| 3,006,003 | 10/1961 | Johnson, Jr. . |
| 3,076,904 | 2/1963 | Kleesattel et al. . |
| 3,086,288 | 4/1963 | Balamuth et al. . |
| 3,184,353 | 5/1965 | Balamuth et al. . |
| 3,346,279 | 10/1967 | Stachiw et al. . |
| 3,401,446 | 9/1968 | Obeda et al. . |
| 3,526,219 | 9/1970 | Balamuth . |
| 3,589,363 | 6/1971 | Banko et al. . |
| 3,683,736 | 8/1972 | Loose . |
| 3,693,613 | 9/1972 | Kelman . |
| 3,710,641 | 1/1973 | Anderson . |
| 3,809,977 | 5/1974 | Balamuth et al. . |
| 3,823,717 | 7/1974 | Pohlman et al. . |
| 3,862,630 | 1/1975 | Balamuth . |
| 3,899,166 | 6/1975 | Scurlock . |
| 3,902,495 | 9/1975 | Weiss et al. . |
| 3,990,452 | 11/1976 | Murry et al. . |
| 4,041,947 | 8/1977 | Weiss et al. . |
| 4,056,761 | 11/1977 | Jacoby et al. . |
| 4,063,557 | 12/1977 | Wuchinich et al. . |
| 4,184,510 | 1/1980 | Murry et al. . |
| 4,188,952 | 2/1980 | Loschilov et al. . |
| 4,248,232 | 2/1981 | Engelbrecht et al. . |
| 4,277,710 | 7/1981 | Harwood et al. . |

(List continued on next page.)

Primary Examiner—Robert A. Hafer
Assistant Examiner—David J. Kenealy
Attorney, Agent, or Firm—Knobbe, Martens, Olson & Bear

[57] ABSTRACT

Disclosed is a method and apparatus for removing a polymethylmethacrylate or other cement plug from the medullary canal during hip-revision surgery. In accordance with the method, a portion of the PMMA plug is softened and a plug removal tool is advanced through the softened portion to become imbedded in the plug. The plug is permitted to harden around the tool, and the tool is withdrawn thereby pulling the plug with it. Softening may be accomplished by conducting ultrasonic energy through the removal tool tip, or by other means. Hardening is accomplished by removing the heat source and permitting passive cooling of the material, or by accelerating cooling of the material through the use of a heat sink or a circulating media such as a compressed gas. Also disclosed is a self-cooling tool tip.

11 Claims, 20 Drawing Sheets

U.S. PATENT DOCUMENTS

| | | |
|---|---|---|
| 4,298,074 | 11/1981 | Mattchen . |
| 4,418,583 | 12/1983 | Taig . |
| 4,425,115 | 1/1984 | Wuchinich . |
| 4,636,219 | 1/1987 | Pratt et al. . |
| 4,679,959 | 7/1987 | Cavallaro . |
| 4,686,971 | 8/1987 | Harris et al. . |
| 4,705,038 | 11/1987 | Sjostrom et al. . |
| 4,705,500 | 11/1987 | Reimels et al. . |
| 4,750,488 | 6/1988 | Wuchinich et al. . |
| 4,760,845 | 8/1988 | Kovalcheck .................... 128/398 |
| 4,768,496 | 9/1988 | Kreizman et al. . |
| 4,778,469 | 10/1988 | Lin et al. . |
| 4,781,507 | 11/1988 | Duenas . |
| 4,783,969 | 10/1989 | Huebsch ....................... 606/92 |
| 4,828,566 | 5/1989 | Griss . |
| 4,832,683 | 5/1989 | Idemoto et al. . |
| 4,834,081 | 5/1989 | Van Zile . |
| 4,846,161 | 7/1989 | Roger . |
| 4,850,755 | 7/1989 | Spencer et al. . |
| 4,919,153 | 4/1990 | Chin ............................ 606/93 |
| 4,950,266 | 8/1990 | Sinofsky ....................... 606/7 |
| 5,019,083 | 5/1991 | Klapper et al. . |
| 5,027,792 | 7/1991 | Meyer .......................... 606/46 |
| 5,037,442 | 8/1991 | Wintermantel ................ 623/22 |
| 5,041,120 | 8/1991 | McColl ......................... 606/92 |
| 5,163,933 | 11/1992 | Grundfest ..................... 606/99 |
| 5,284,484 | 2/1994 | Hood ............................ 606/99 |
| 5,330,481 | 7/1994 | Hood ............................ 606/99 |

FOREIGN PATENT DOCUMENTS

| | | |
|---|---|---|
| 121491 | 3/1983 | European Pat. Off. . |
| 133393 | 2/1985 | European Pat. Off. . |
| 243298 | 4/1986 | European Pat. Off. . |
| 2614524 | 4/1987 | France . |
| 1371335 | 10/1974 | United Kingdom . |
| 659798 | 3/1977 | U.S.S.R. . |
| 929088 | 5/1982 | U.S.S.R. . |
| 1229467 | 8/1984 | U.S.S.R. . |
| 8802250 | 4/1988 | WIPO . |

OTHER PUBLICATIONS

"Theory and Analysis of Sectional Concentrators" by L. G. Merkulov and A. V. Kharitonov, Apr. 18, 1958.

"Mechanical Transformers for Producing Very Large Motion" by E. A. Neppiras, Acustica, vol. 13, Mar. 26, 1963.

"Complete Replacement Arthroplasty of the Hip by the Ring Prosthesis", The Journal of Bone and Joint Surgery, P. A. Ring, pp. 720–731 (British) vol. 50B, No. 4, Nov. 1968.

"Ultrasonic Cataract Extraction With Acoustic Horn" by Douglas McG. Clarkson and Calbert I. Phillips, Transactions Of The Ophthalmological Society Of The United Kingdom (1975) 95,477.

"Femoral Fractures in Conjunction With Total Hip Replacement" by Richard D. Scott, et al., The Journal Of Bone And Joint Surgery, vol. 57–A, No. 4, Jun. 1975.

"A Sonic Tool for Spinal Fusion" by Edmund B. Weis, Jr., M.D., Orthopedic Clinics Of North America, vol. 8, No. 1, Jan. 1977.

Orthopedic Catalog–Richards Manufacturing Co., Inc., pp. 10, 14 and 20, 1981.

"A New Technique for Removal of Broken Femoral Stems in Total Hip Replacement" by William H. Harris, et al., The Journal of Bone and Joint Surgery, vol. 63–A, No. 5, Jun. 1981.

"Piezoelectric Ceramics: Characteristics and Applications" by Don Berlincourt, Acoustical Society of America, vol. 70, No. 6, Dec. 1981.

"A Model System to Demonstrate the Role of Cavitational Acitivity in Ultrasonic Scaling" by A. D. Walmsky; W. R. E. Larid and A. R. Williams, J. Dent Res 63(9): 1162–1165, Sep. 1984.

Biological Fixation of the Porocaot AML® Hip–Manual for Pre–Operative Planning and Recommended Surgical Technique (1984) by Charles A. Engh, M.D. and J. Dennis Bobyn, Ph.D.

"Posterior Lumbar Interbody Fusion Technique: Complications and Pitfalls" by Paul M. Lin, M.D., Clinical Orthopaedics and Related Research, No. 193, Mar. 1985.

"The Stepped Horn" by John F. Belford–Clevite Electronic Components Division of Clevite Corporation, Dec. 12, 1985.

Technical Support Package on "Quick–Connect Heavy–Duty Fastener", NASA Tech Brief, vol. 10, No. 2, Item #34, Mar./Apr. 1986.

"Atraumatic Removal of a Well–Fixed Porous Ingrowth Hip Prostehesis" by Shearwood J. McClelland, et al., Orthopaedic Review, vol. XV, No. 6, Jun. 1986.

"The Window Technique for the Removal of Broken Femoral Stems in Total Hip Replacement" by John R. Moreland, et al., Clinical Orthopaedics and Related Research, No. 212, Nov. 1986.

OTHER PUBLICATIONS

"Development of a Bone-Fixation Prosthetic Attachment" by Lester J. Owens, NASA Kennedy Space Center, pp. 281, 283, 285, 287, 289, 291 and 293.

Technical Support Package for Tech Brief LA-R-12232, "Quick-Connect Threaded Attachment Joint", Langley Research Center, NASA.

"Work-in-Progress #1: The Lithotriptor and Its Potential Use in the Revision of Total Hip Arthroplasty" by Robert R. Karpman, et. al., Orthopaedic Review, vol. XVI, No. 1, Jan. 1987.

"Controlled Perforation: A Safe Method of Cement Removal from the Femoral Canal" by Sam V. Sydney, et al., Surgical Rounds For Orthopaedics, pp. 17-19, Jan. 1989.

"Proximal Femoral Osteotomy in Difficult Revision Hip Surgery: How to Revise the Unrevisable" Hugh H. Cameron, Ph.D., Contemporary Orthopaedics, May 1989, vol. 18, No. 5.

"Symposium: Advanced Biomaterials-The Future of Orthopaedics" by John P. Collier, D. E.; Charles A. Engh, M. D.; Jack Lemons, Ph.D., Contemporary Orthopaedics, Aug. 1989, vol. 19, No. 2.

"Femoral Fracture During Non-Cemented Total Hip Arthroplasty", John A. Schwartz, Jr., et al., The Journal Of Bone And Joint Surgery, Incorporated, pp. 1135-1142, Sep. 1989, vol. 71-A, No. 8.

"Effect of Press-Fit Femoral Stems on Strains in the Femur: A Photoelastic Coating Study", X. M. Zhou, et al., The Journal Of Arthroplasty, Mar. 1990, vol. 5, No. 1A.

"The Use of Ultrasonic Tools In Revision Arthroplasty Procedures", Contemporary Orthopaedics by Robert C. Klapper, M.D. and James T. Caillouette, M.D., Mar. 1990, vol. 20, No. 3.

Piezoceramics Applications Data (Undated), pp. 3-10.

"Piezoelectric Displacement Generators-Status and Low Frequencies" by D. Berlincourt, Channel Industries, Inc. (Undated).

*Fracture Appliances* by DePuy, Inc., 1964.

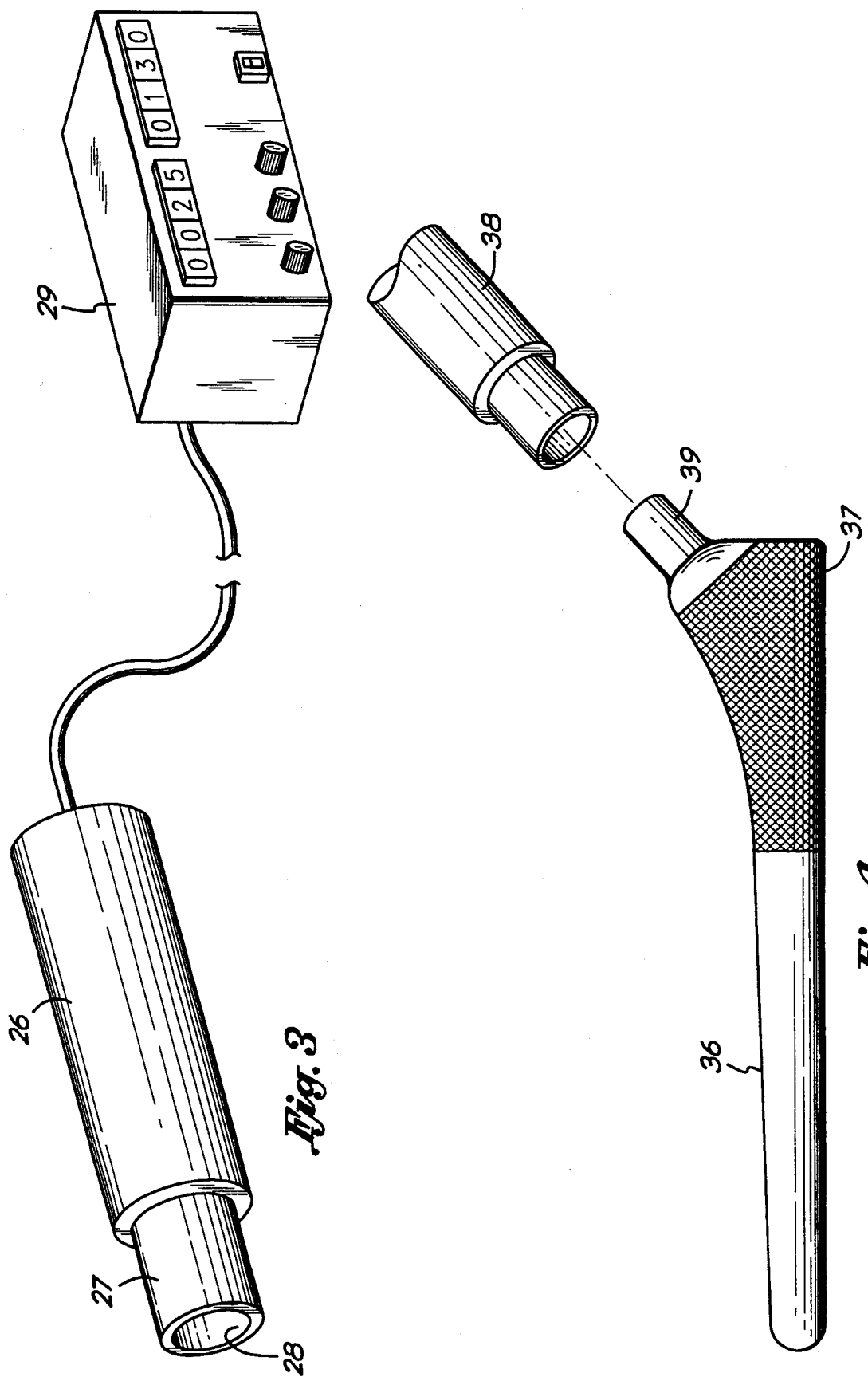

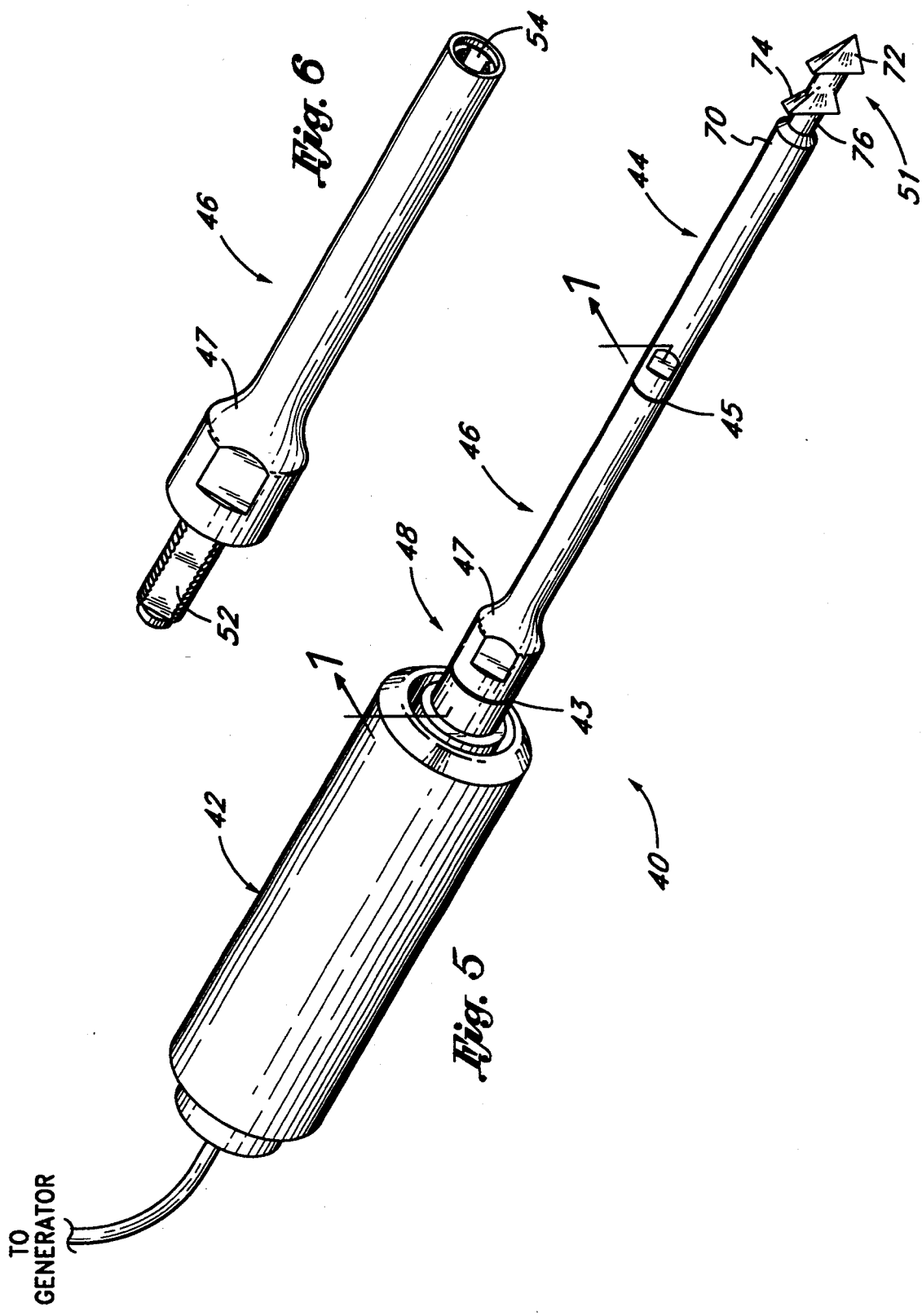

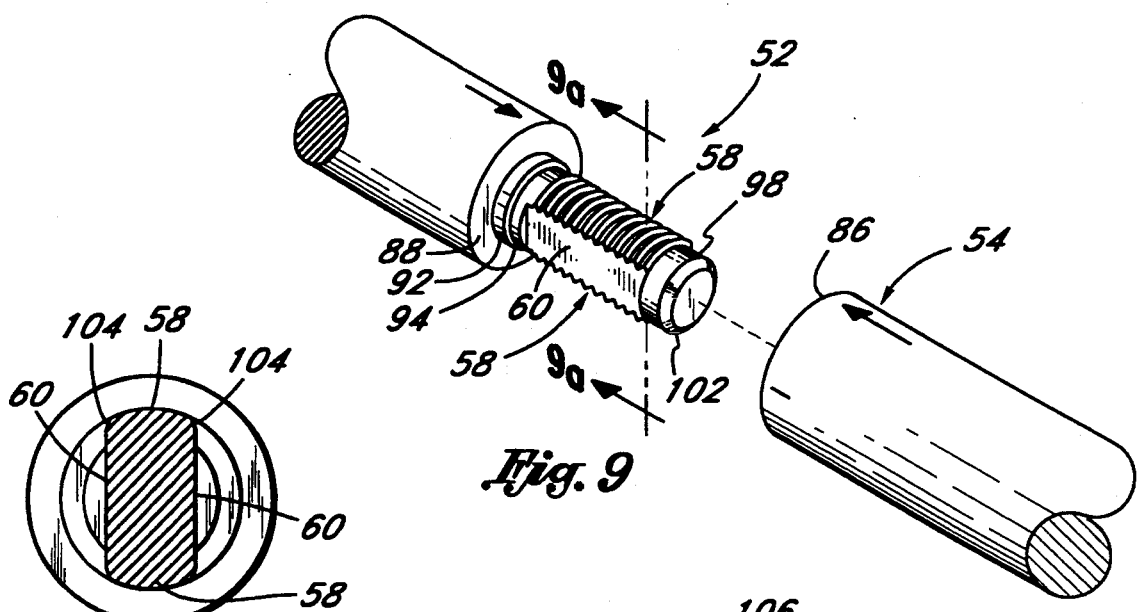
Fig. 9
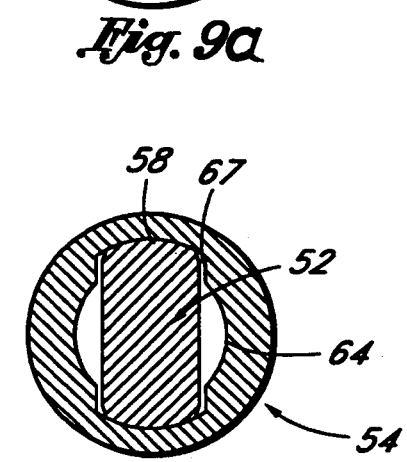
Fig. 9a
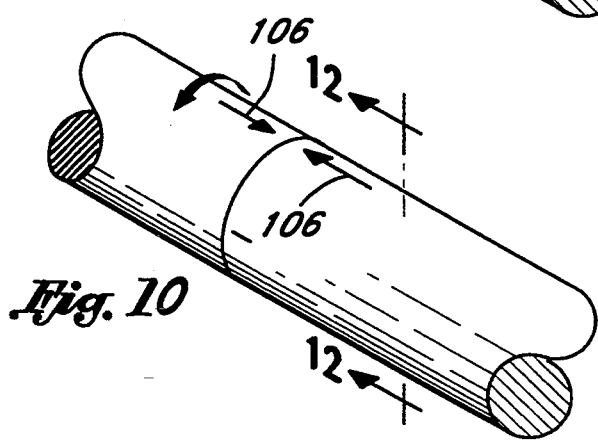
Fig. 10
Fig. 12
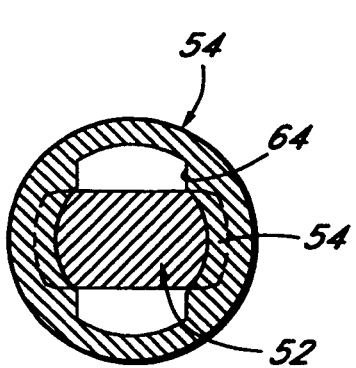
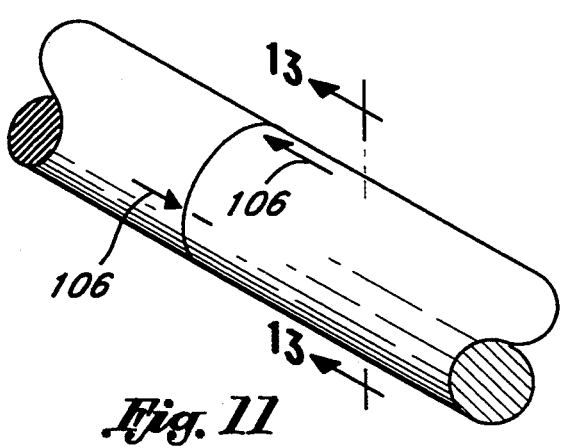
Fig. 13
Fig. 11

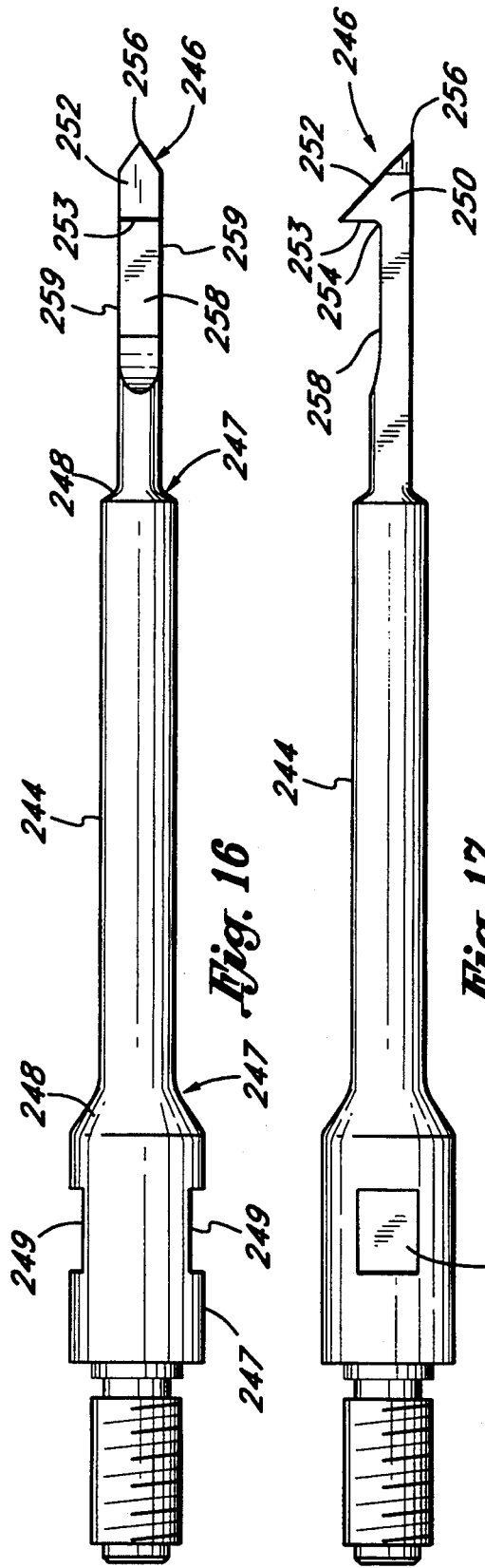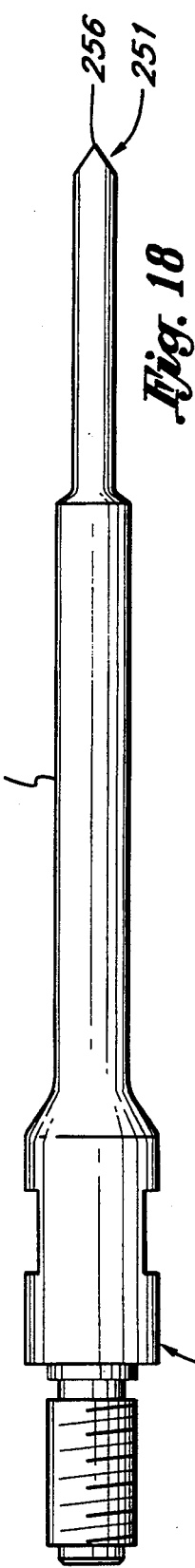
Fig. 16  Fig. 17  Fig. 18  Fig. 19  Fig. 20

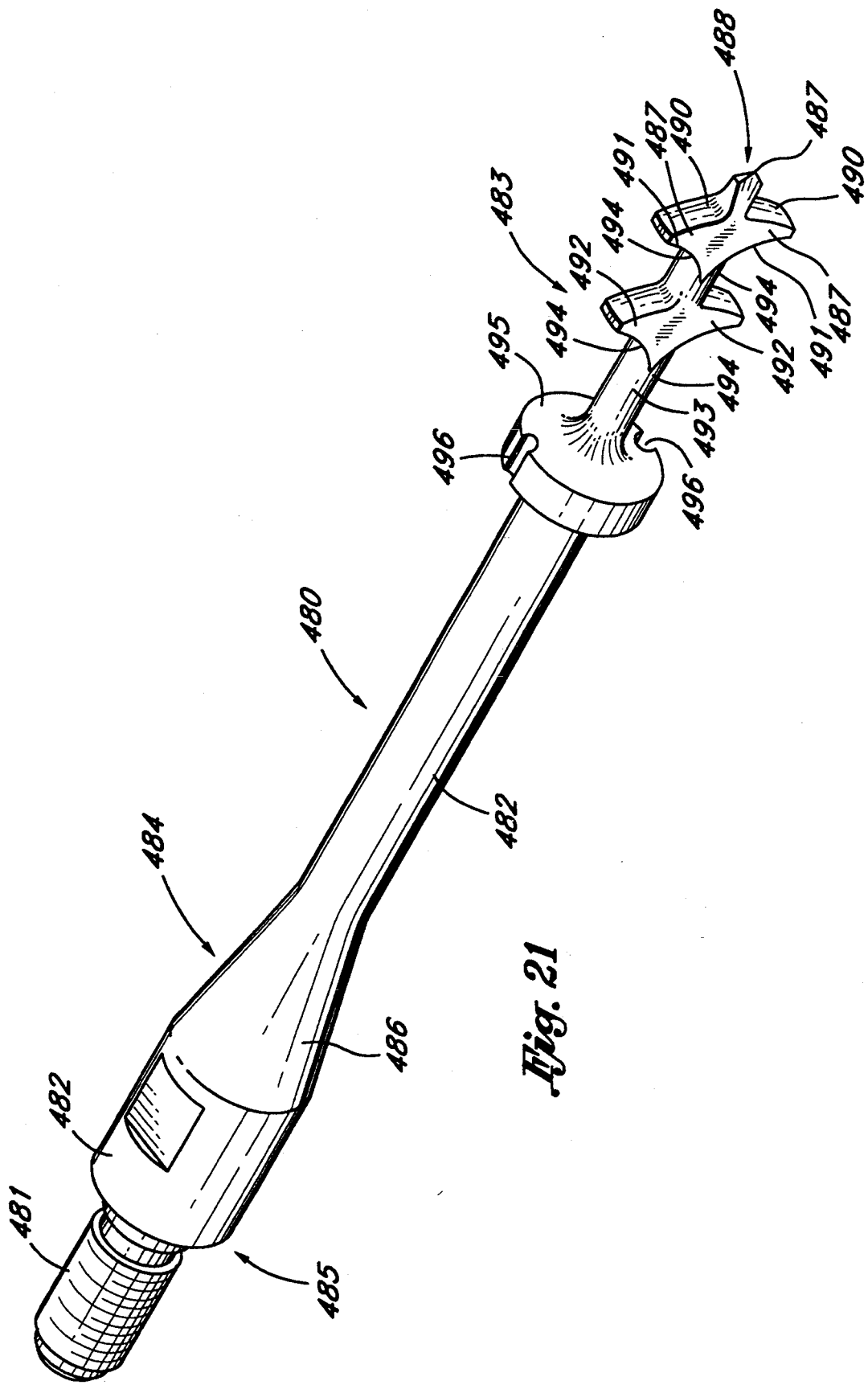

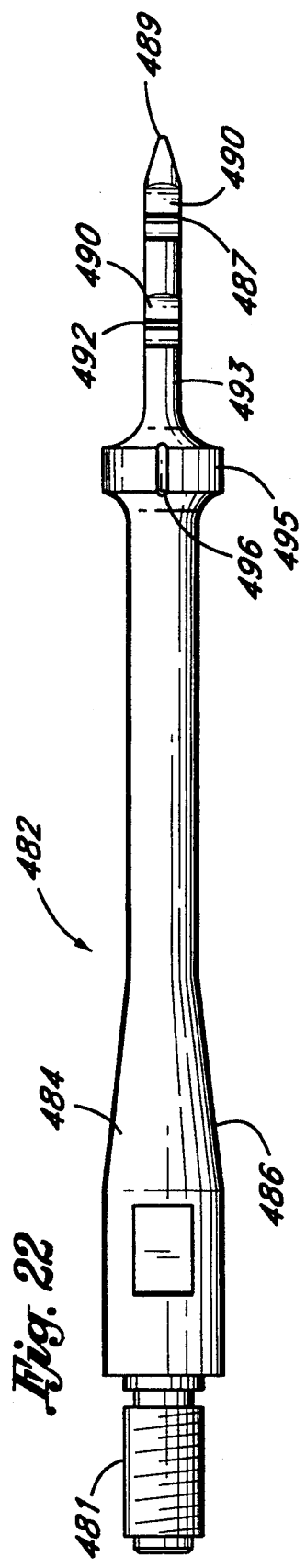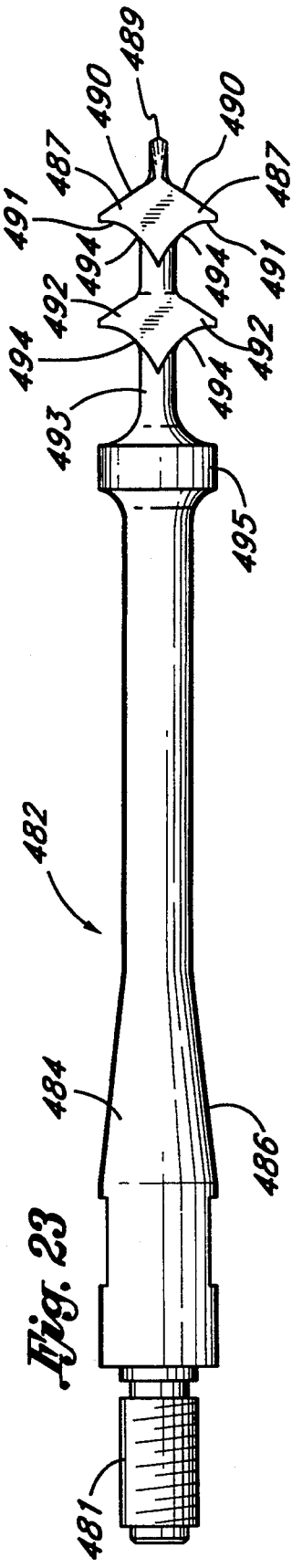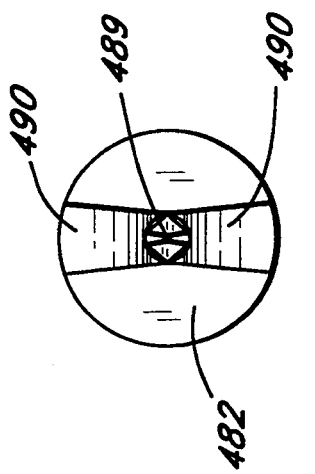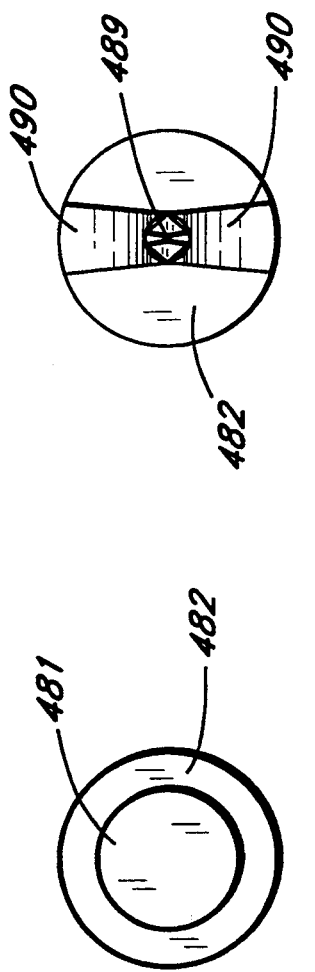

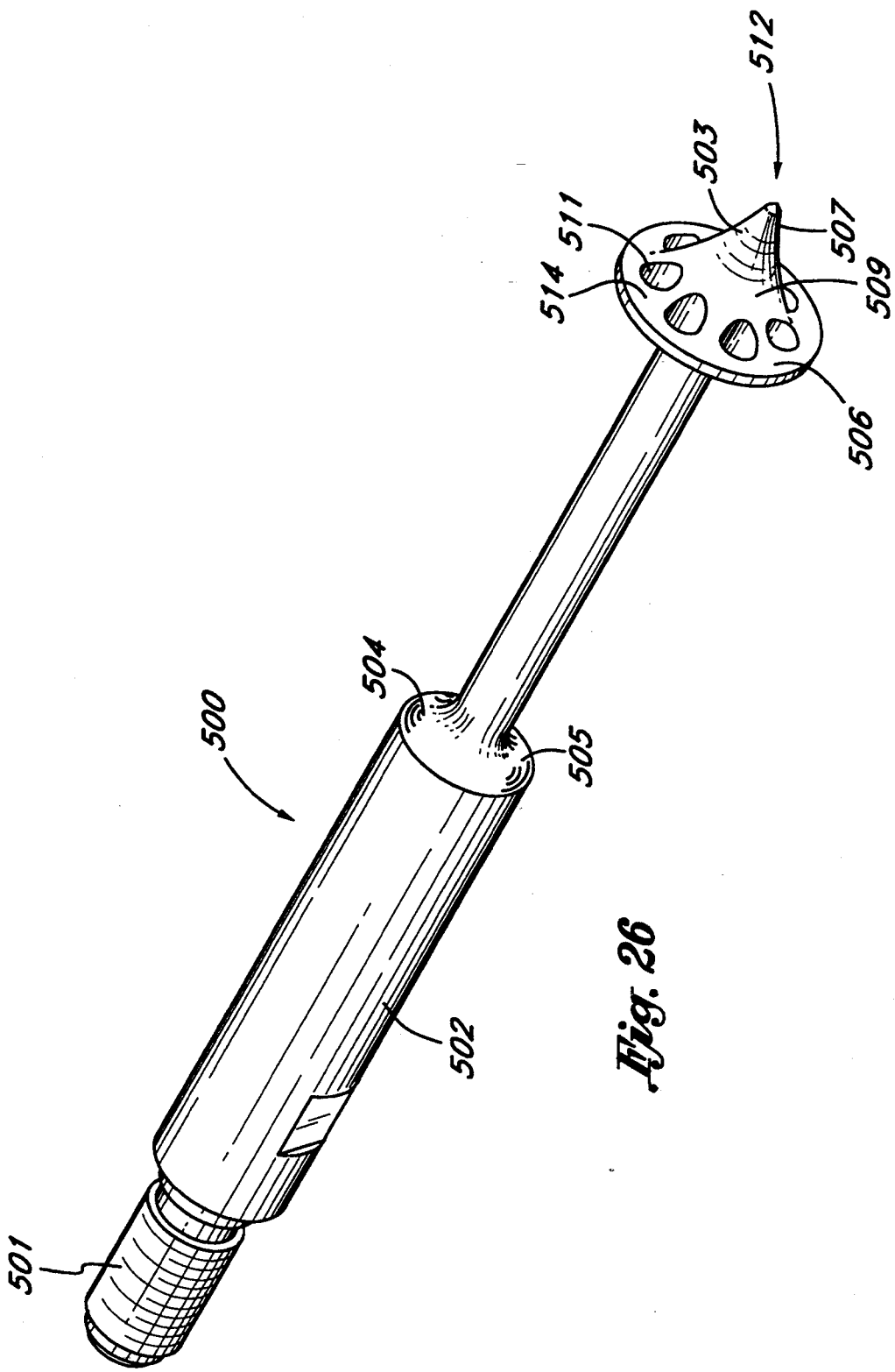

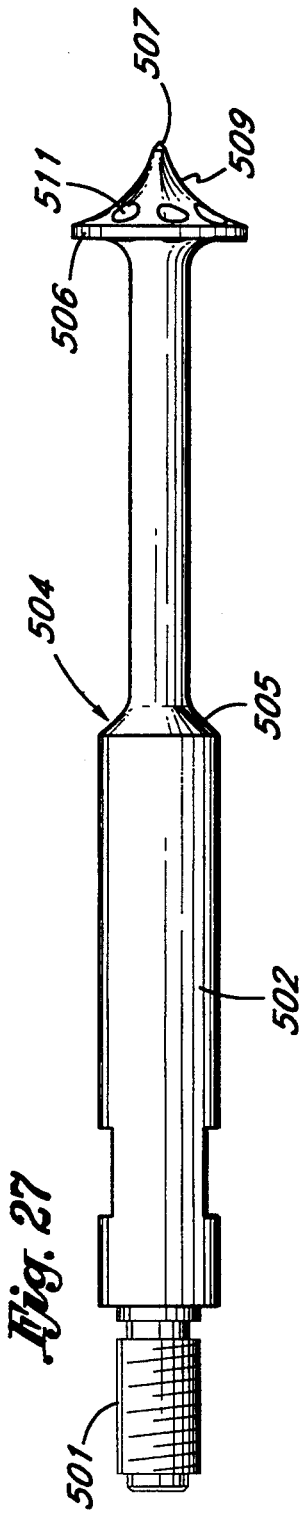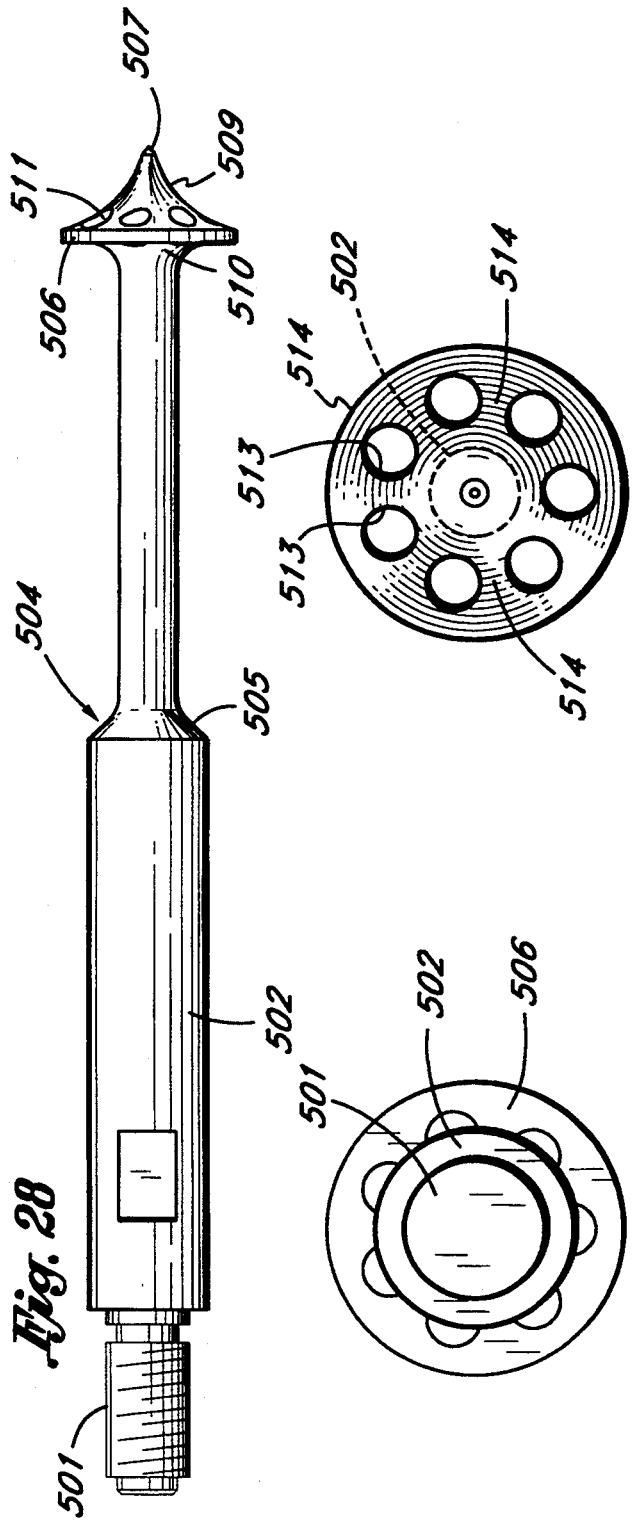

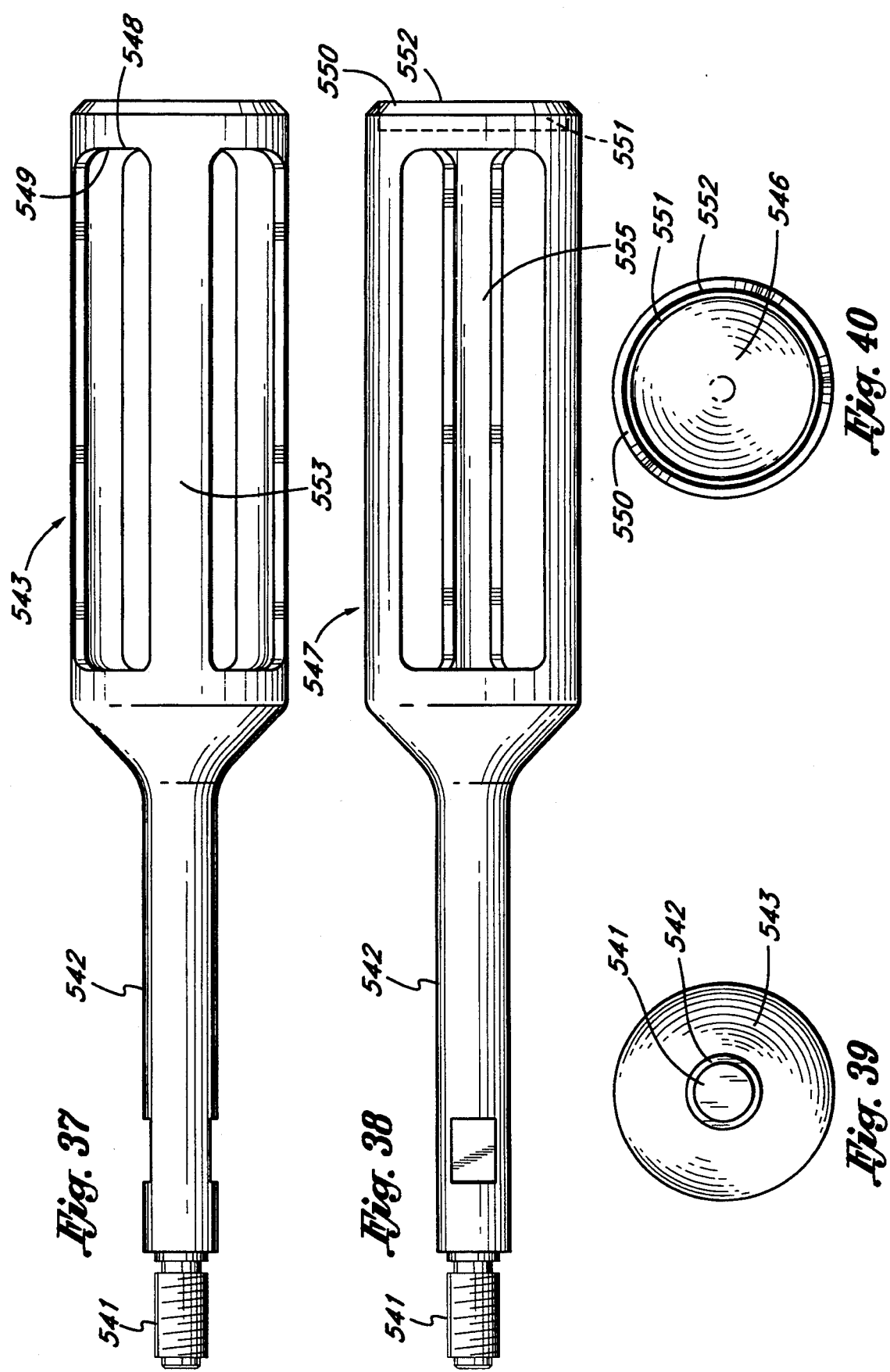

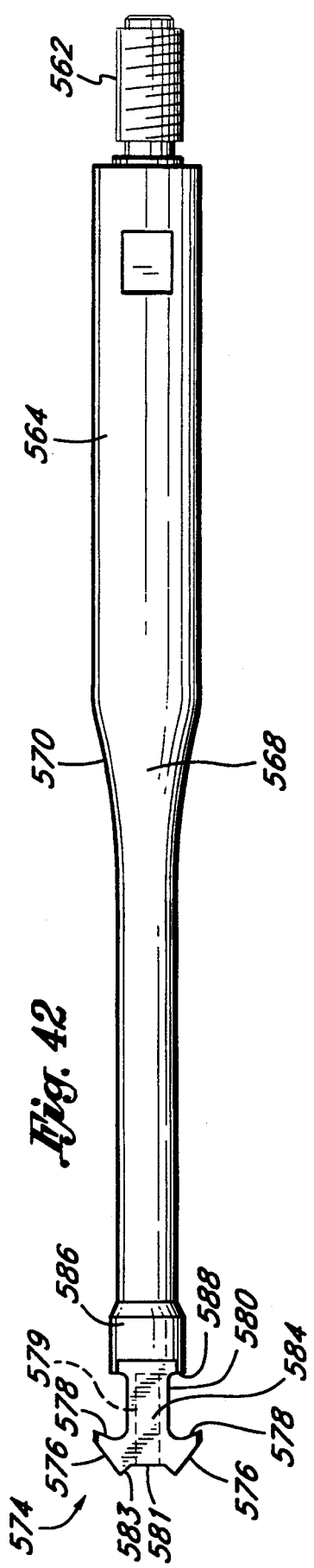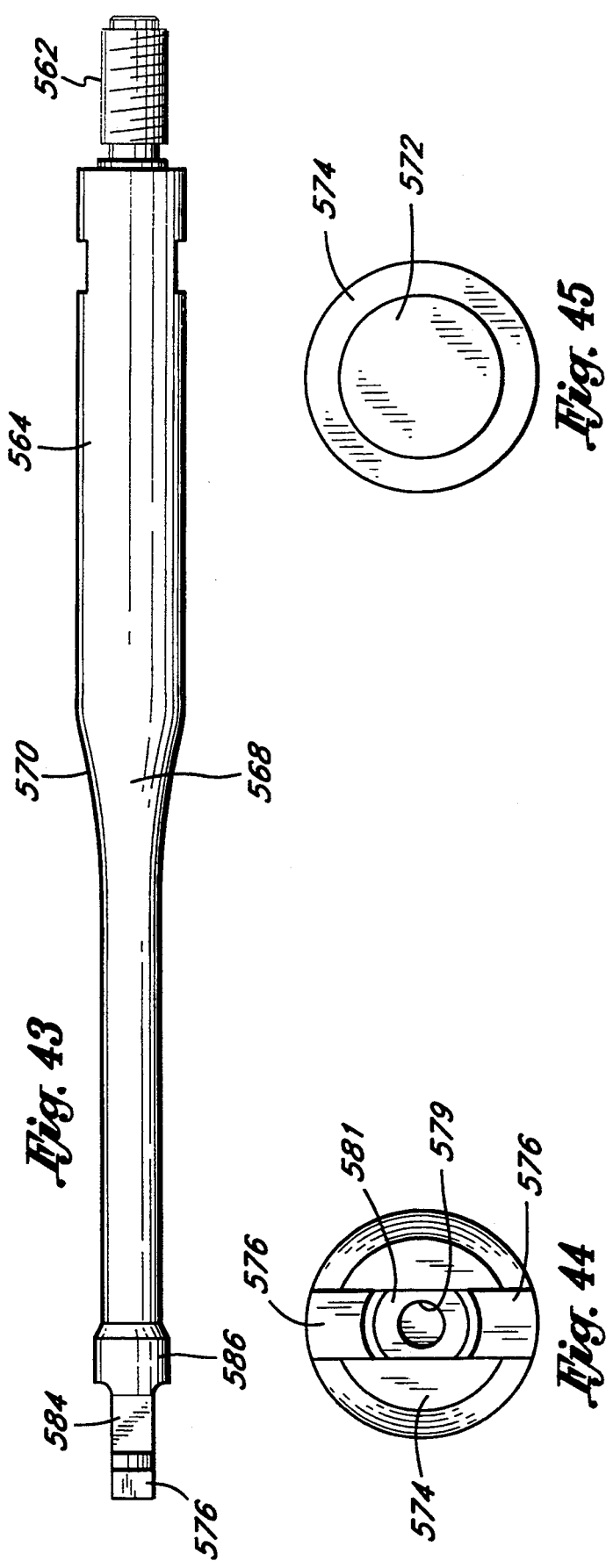

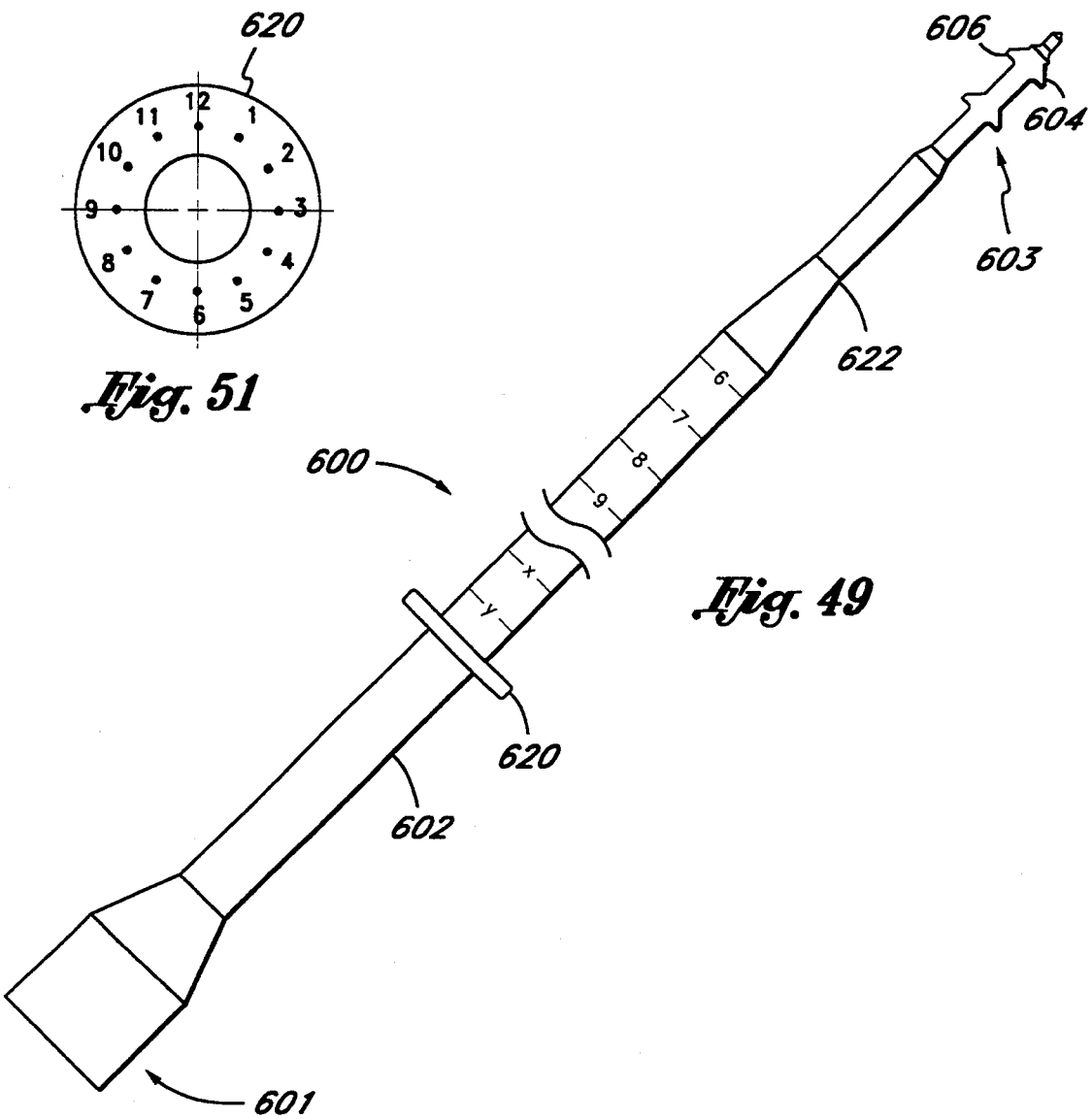
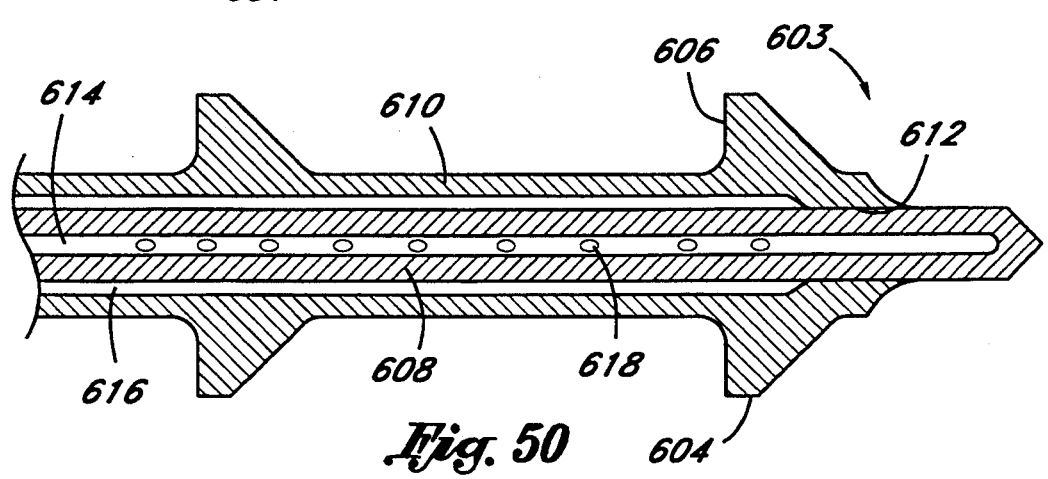

PLUG PULLING METHOD

RELATED APPLICATIONS

The present application is a continuation-in-part of copending application Ser. No. 713,959, filed Jun. 11, 1991, which is a continuation-in-part of application Ser. No. 665,418, filed Mar. 5, 1991 which is a continuation-in-part of Ser. No. 304,820, filed Jan. 31, 1989, now U.S. Pat. No. 5,019,083, issued May 28, 1991.

FIELD OF THE INVENTION

This invention relates to techniques and apparatus for introducing and removing an orthopedic prosthesis such as a femoral component of a hip joint replacement, acetabular cup, knee joint, shoulder joint, or the like. More particularly, the present invention relates to a method of removing a polymethylmethacrylate or other cement plug from the distal end of the medullary canal during revision surgery.

BACKGROUND OF THE INVENTION

It has been over sixty years since the first use of replacement parts for hip joints. There have been many advances in the prosthetic components, materials, surgical techniques and the like, so that total hip joint replacement has become relatively commonplace. Related techniques have also been used for replacing knee and shoulder joints.

There are two principal components to a hip replacement prosthesis. One is an acetabular cup which is implanted in the acetabulum. The acetabular cup provides a spherical socket which is the bearing surface for the replacement joint. The other component comprises a femoral stem which is fitted into the medullary canal of the femur and a femoral head on the steam having a spherical surface which meets with the acetabular socket.

The femoral portion of the prosthesis is inserted by cutting off the femoral neck with or without removing the greater trochanter. The medullary canal is then prepared using drills, reamers and successively larger rasps to produce a cavity which is closely complementary to the femoral stem. After cleaning, the femoral stem is driven into place in the canal with what is essentially a press fit. Preparing the cavity to fit the stem is tedious and prolongs the period the patient must be kept under anaesthesia.

The femoral stem may be held in place by a polymethylmethacrylate cement (PMMA) or it may be provided with a porous surface on the shank which accommodates ingrowth of cancellous bone which secures the femoral component in the femur.

The acetabular cup is implanted after grinding a socket in the pelvis to receive it. The acetabular cup may be secured with cement, or may be fastened to the bone with screws after a press fit. Similar techniques, differing in detail are used for implanting replacement shoulder joints, knees and the like.

Despite advances in the technology of hip replacement, it is found that a substantial number of "revisions" are required. Such revisions involve removing components of the hip joint and replacing them. Such revisions may be required shortly after the original surgery due to complications. More commonly they occur eight or ten years after the original surgery due to any of a number of problems that may arise. Such revisions are traumatic for the patient, tedious for the surgeon, and quite time consuming for surgical staff and facilities.

A principal problem in revisions is removal of the femoral component. Some such components are made with transverse holes or threaded holes for connection of tools to extract the femoral stem from the medullary canal. Repeated hammer blows may be applied for driving the stem out of the cavity. Sometimes a window is cut in the femoral cortex near the distal end of the shank, and a punch and hammer are used for driving the shank toward the open end of the femur. Trauma to the patient can be severe and breakage of parts of the femur is not unusual. The techniques employed for removing the femoral component have been characterized as barbaric.

Another technique that has been attempted is removal of the polymethylmethacrylate with an ultrasonically vibrated osteotome. Such a technique is described in U.S. Pat. No. 4,248,232 by Engelbrecht. The osteotome is used for scooping out polymethylmethacrylate cement softened by the ultrasonic vibrations.

Other techniques involve use of long, thin osteotomes for cutting either the cement used for securing the prosthesis in the medullary canal or cancellous bone in the case of an ingrowth prosthesis. In effect, the osteotomes are long chisels which are tapped to disintegrate the cancellous bone or cement and free the prosthesis from the surrounding cortex. For example, in a paper entitled "Atraumatic Removal of a Well-Fixed Porous Ingrowth Hip Prosthesis, " *Orthopedic Review*, Vol 15, No. 5, Jun. 1986, page 387, Doctors McClelland, James and Simmons describe removal of a femoral component "by the use of an oscillating saw and long, thin osteotomes to carefully separate the prosthesis from its intra-medullary environment. This portion of the procedure was both tedious and somewhat time-consuming, but no iatrogenic damage to the cortical tube of the proximal femur resulted. After the proximal half of the prosthesis had been freed up in this manner, the prosthesis was then extractable, using multiple heavy hammer blows applied to vise grips attached to the end of a McReynolds-wedge extractor."

Another difficulty encountered during revision surgery involves removal of the cement "plug" from the medullary canal. Typically, the initial cavity formed in the medullary canal is deeper than the length of the femoral portion of the prosthesis. The area surrounding the femoral stem and between the distal end of the femoral stem and the end of the medullary canal is filled with cement during initial implantation.

Prior art methods for removing the cement plug from the distal end of the canal include drilling through the cement to either tap the hole with a female thread or to engage a hook around the rear surface of the plug. However, the relative hardness of the cement compared to the bone creates a risk that the drill will migrate to the side and perforate the bone. In addition, progress of the drill is generally observed using x-ray visualization.

It is clear that faster and less traumatic techniques are desirable for removing components of prostheses inserted in the medullar canal. In addition, there remains a need for an improved method of removing the cement plug from the distal end of the medullary canal which reduces the risk of wall perforation and which can be accomplished without the use of x-ray visualization.

SUMMARY OF THE INVENTION

There is provided in accordance with one aspect of the present invention a method of removing a deposit of non-biological material from a bone cavity. Non-biological materials of the type removable in accordance with the present method are those which are convertible between a relatively hard state and a relatively softened state, including bone cements such as PMMA.

In accordance with the method of the present invention, a deposit of non-biological material is identified in a bone cavity. At least a portion of the non-biological material is converted from a first hardened state to a second softened state. Thereafter, a removal tool is advanced into the softened portion of the non-biological material. The softened portion of non-biological material is permitted to return to the first hardened state, and the removal tool is thereafter removed, thereby withdrawing the non-biological material from the bone cavity. Preferably, the non-biological material comprises cement, and, preferably, polymethylmethacrylate.

In one embodiment of the invention, the non-biological material is converted from the first hardened state to the second softened state by the application of heat. Application of heat to the non-biological material is preferably accomplished by conducting heat from the removal tool to the non-biological material. Heat is preferably generated by ultrasonic vibration of the removal tool, or by an electric current. Alternatively, heat is transmitted by conducting light through a fiber optic waveguide. As a further alternative, the non-biological material may be softened by the application of a softening agent which comprises a solvent for the non-biological material.

In accordance with a further aspect of the present invention, there is provided a method of removing a deposit of cement from a bone, said cement of the type which is convertible from a first hardened state to a second softened state by the application of heat. In accordance with the method, an ultrasonic energy activated tool of the type adapted for coupling to an ultrasonic transducer is provided. The tool has a first connection end and a second working tip end.

The first connection end of the tool is coupled to an ultrasonic energy transducer, and the second working tip of the tool is contacted either before or after activation of the ultrasonic energy transducer, with the cement deposit to be removed. At least a portion of the working tip is advanced into the cement while the ultrasonic energy transducer is activated. Thereafter, the cement is permitted to harden around the working tip, and the tool is withdrawn from the bone cavity thereby withdrawing the cement deposit.

Preferably, the permitting the cement to harden step comprises contacting the cement with a heat sink for conducting heat therefrom. Alternatively, the hardening step may be facilitated by contacting the cement with a coolant, such as compressed carbon dioxide.

In accordance with a further aspect of the present invention, there is provided a method for removing a deposit of polymethylmethacrylate from the distal end of the medullary cavity in a femur, during hip-joint revision surgery. The method comprises the steps of contacting the polymethylmethacrylate deposit with a removal tool and heating the portion of polymethylmethacrylate which is in contact with the removal tool. The removal tool is thereafter advanced into the heated polymethylmethacrylate. The polymethylmethacrylate is thereafter permitted to solidify around the removal tool, and the removal tool is withdrawn thereby withdrawing the solidified polymethylmethacrylate deposit.

Heating is preferably accomplished by the application of ultrasonic energy to the removal tool, or by conducting an electric current through at least a portion of the removal tool. Preferably, the removal tool comprises a distal working tip having a cross-sectional area through at least a portion thereof which is greater than the cross-sectional area through at least a portion of the tool on the proximal side of the distal working tip.

These and other features and advantages of the present invention will become apparent from the detailed description of preferred embodiments which follows, when considered together with the attached drawings and claims.

BRIEF DESCRIPTION OF THE DRAWINGS

FIG. 3 is a schematic view of a medical device including a power supply and an ultrasonic transducer equipped for coupling to a femoral component as illustrated in FIG. 2;

FIG. 4 is a side view of a femoral component including rasp-like teeth;

FIG. 5 is a schematic illustration of an ultrasonic medical tool of the present invention showing a handpiece, an extender and a cement plug removal tool bit;

FIG. 6 is a perspective view of the extender of FIG. 5;

FIG. 7 is a partial cross-sectional view of the ultrasonic medical tool of FIG. 5 taken along line 7—7 illustrating two junctions of the present invention;

FIG. 9 is an exploded perspective view of one of the junctions of FIG. 7, illustrating the generally cylindrical male component on the proximal end of a surgical tool having a pair of splines interrupted by a pair of flats;

FIG. 9a is a cross-sectional view of the junction of FIG. 9 taken along line 9a—9a.

FIG. 10 is an assembly perspective view of the junction of FIG. 9 with a male component inserted into a female component;

FIG. 11 is an assembly perspective view of the junction of FIG. 10 with the components rotated to engage corresponding splines of each component;

FIG. 12 is a cross-sectional view of the junction of FIG. 10 taken along lines 12—12;

FIG. 13 is a cross-sectional view of the junction of FIG. 11 taken along lines 13—13;

FIG. 16 is a top plan view of the tool bit of FIG. 15;

FIG. 17 is a side elevational view of the tool bit of FIG. 15;

FIG. 18 is a bottom plan view of the tool bit of FIG. 15;

FIG. 19 is a left end view of the tool bit of FIG. 18;

FIG. 20 is a right end view of the tool bit of FIG. 18;

FIG. 21 is a perspective view of a plug puller tool bit of the present invention;

FIG. 22 is a plan view of the plug puller tool bit of FIG. 15;

FIG. 23 is a side view of the plug puller tool bit of FIG. 15;

FIG. 24 is a left end view of the plug puller tool bit of FIG. 23;

FIG. 25 is a right end view of the plug puller tool bit of FIG. 23;

FIG. 26 is a perspective view of a disk drill of the present invention;

FIG. 27 is a plan view of the disk drill of FIG. 26;

FIG. 28 is a side view of the disk drill of FIG. 26;

FIG. 29 is a left end view of the disk drill of FIG. 28;

FIG. 30 is a right end view of the disk drill of FIG. 28;

FIG. 37 is a plan view of the trephine of FIG. 36;

FIG. 38 is a side view of the trephine of FIG. 36;

FIG. 39 is a left end view of the trephine of FIG. 38;

FIG. 40 is a right end view of the trephine of FIG. 38;

FIG. 42 is a plan view of the poly-plug puller tool bit of FIG. 41;

FIG. 43 is a side view of the poly-plug puller tool bit of FIG. 41;

FIG. 44 is a left end view of the poly-plug puller tool bit of FIG. 42;

FIG. 45 is a right end view of the poly-plug puller tool bit of FIG. 42;

FIG. 49 is a schematic view of a self cooling plug removal tip;

FIG. 50 is a sectional view of an enlargement of the distal portion of the removal tip FIG. 49; and FIG. 51 is an end view of an abutment on the removal tip of FIG. 49.

DETAILED DESCRIPTION OF PREFERRED EMBODIMENTS

Figures 1, 2:
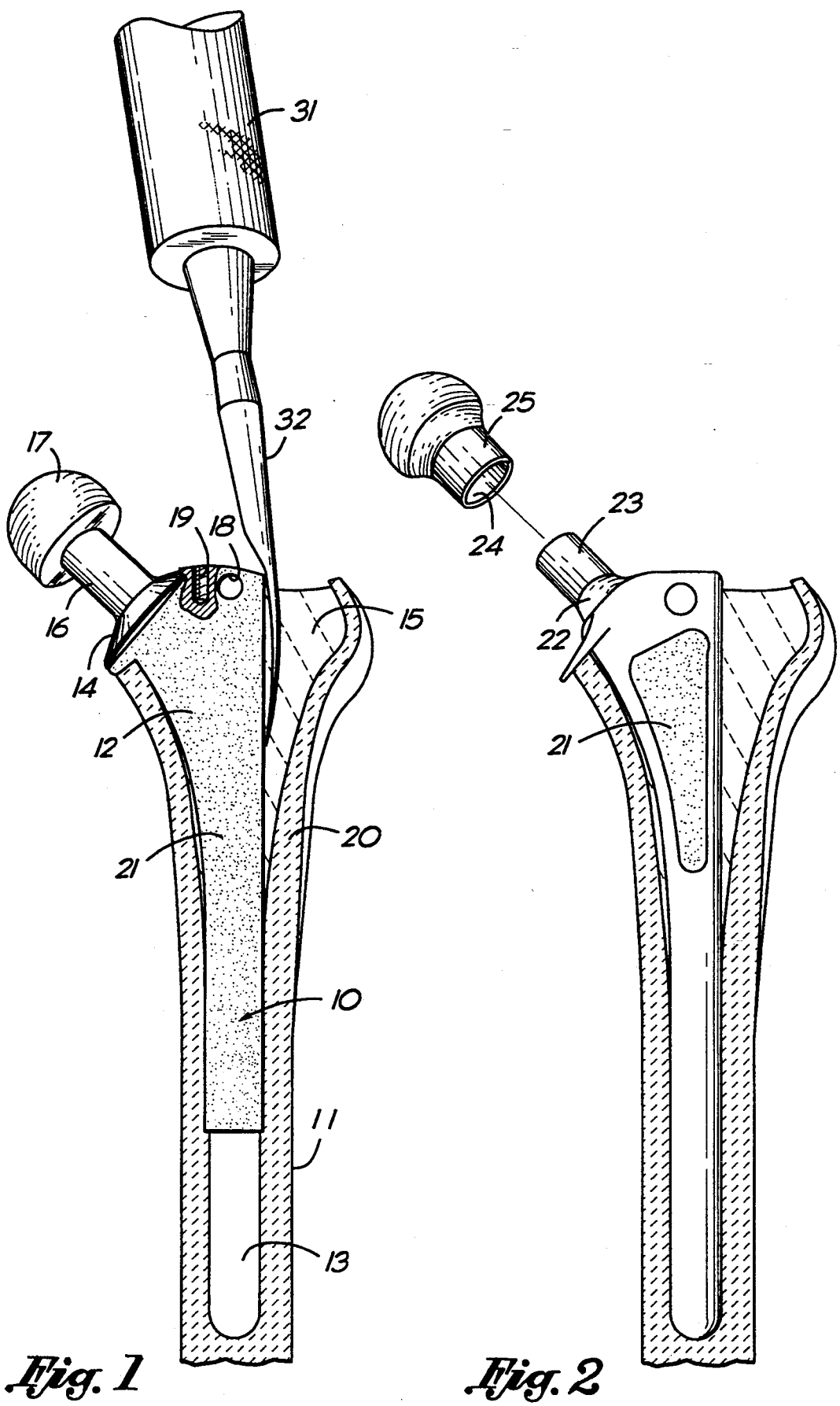
FIG. 1 is a side view partly in cross section of an exemplary femoral implant component of a hip replacement joint as implanted in a femur with an osteotome for disrupting cancellous bone.
FIG. 2 is a side view of another embodiment of a femoral component of a hip replacement joint implanted in a femur, with the head of the component exploded from the body.
Figure 2:
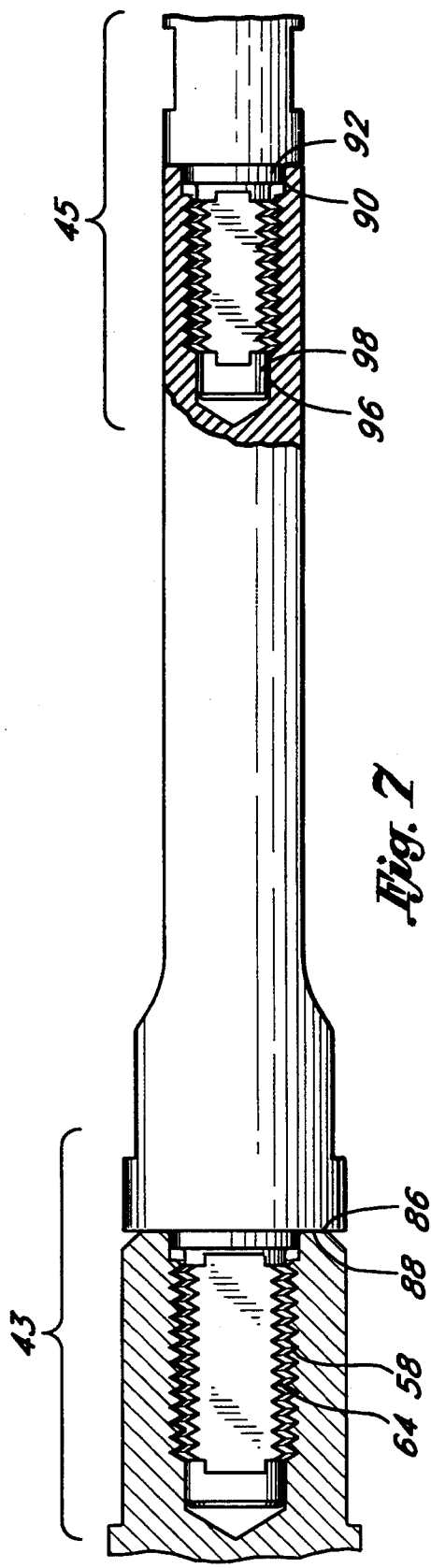

FIG. 1 illustrates an exemplary femoral component 10 of a hip prosthesis joint implanted in the end of a femur which has the trochanter osteotomized. The body 12 of the prosthesis and at least a portion of the shank 13 which extends along the medullary canal have a porous surface. Such a porous surface is provided on the prosthesis by some manufacturers in the form of metal beads having the same composition as the prosthesis which are sintered onto the solid metal of the prosthesis. Other manufacturers employ a mat of metal wires sintered onto the surface. In either type, the porous surface portion provides a substrate into which growth of cancellous bone 15 may occur for rigidly securing the prosthesis to the femur. Some prostheses have a collar 14 which bears against the cortex 20 at the end of the femur. Collarless prostheses are also used.

A neck 16 connects a ball or head 17 to the body of the prosthesis. The spherical head provides the bearing engagement with the acetabular cup (not shown) secured to the patient's pelvis.

A transverse hole 18 extends through the prosthesis for engagement by a tool for extracting the prosthesis from the femur in the event a revision is required. In addition or alternatively, a threaded hole 19 is provided in the end of the body for receiving a tool which can provide a longitudinal force for withdrawing or inserting the prosthesis.

Another type of prosthesis as illustrated in FIG. 2 has a porous surface area 21 on the body for receiving ingrowth of cancellous bone for securing the prosthesis in the medullary canal. In the illustrated embodiment, the neck 22 of the prosthesis has a self-holding taper 23 at its proximal end for receiving a complementary female taper 24 in a head 25 which can thereby be removably secured to the prosthesis. A variety of self-holding tapers with different angles of taper and standard dimensions may be used. These include the Morse, Brown and Sharpe, Jarno, Sellers, Reed, American Standard and Metric tapers. Taper angles of 5% or less are customary. Self-holding tapers cause the shank, when seated firmly in the socket, to tend to stay in place by friction due to the small taper angle. For example, when the head is driven onto a Morse-type taper with a couple of mallet blows, it cannot be removed manually. A larger longitudinal force may be used for separating a self-holding taper.

A removable head for a prosthesis provides the opportunity for stocking heads with varying lengths of neck for fitting to a variety of standard bodies for mixing and matching to fit the prosthesis to an individual patient. For example, up to ten different dimensions of body may be matched with a dozen or so different heads with varying diameters and neck lengths.

For removing a prosthesis implanted in a femur, an ultrasonic transducer 26 (FIG. 3) is coupled to the prosthesis. At the end of the transducer there is a metal sleeve 27 having a socket 28 with a female self-holding taper matching the taper on the neck of the prosthesis. The intimate engagement of the self-holding taper provides high efficiency coupling of the ultrasonic vibrations from the transducer to the prosthesis.

The ultrasonic transducer may be any of a variety of known transducers. These may include electrostrictive, magnetostrictive or electromagnetic devices, as may be preferred by the equipment manufacturer. Each of these has certain advantages depending on the frequency range, amplitude of vibration, and power level.

The ultrasonic transducer is driven by an ultrasonic signal from a conventional power supply 29. Such power supplies typically permit the user to determine the frequency of oscillation and the power level of the ultrasonic signal sent to the transducer. For purposes of disrupting cancellous bone ingrown into the porous surface of a joint prosthesis, a frequency corresponding to a resonant frequency of the prosthesis is desirable for maximizing amplitude of vibration with a given signal strength. Some tuning of frequency for a particular prostheses implanted in bone may be employed in lieu of merely increasing signal strength. It is desirable to employ a frequency in the range of from about 20,000 to 40,000 Hertz, preferably around 25,000 Hertz.

For removing the prosthesis, the transducer is coupled to the self-holding taper on the prosthesis and the prosthesis is ultrasonically vibrated by applying a signal to the transducer. The vibration of the prosthesis disrupts cancellous bone at the surface of the prosthesis due to the impedance mismatch between the metallic prosthesis and the cancellous bone surrounding it. There is a substantial impedance mismatch between the portion of the prosthesis which does not have a porous surface and the surrounding cancellous bone, such as along the length of the shank, and the bone at the interface is readily disrupted. There is less of an impedance mismatch and also less energy transfer at the interface between the porous metal surface and the bony ingrowth. A somewhat higher energy input level is therefore required for disrupting cancellous bone adjacent to the surface of the porous ingrowth area.

After applying ultrasonic vibrations for several seconds, an attempt is made to withdraw the prosthesis. If the transducer is in the way, it may be removed before trying to withdraw the prosthesis to avoid damaging the transducer. In the event the prosthesis is not readily removed by application of pressure or moderate impact, the ultrasonic signal strength can be increased to try again to see if there has been adequate disruption of the cancellous bone at the interface with the porous surface.

Alternatively, the disruption of cancellous bone by the ultrasonic vibrations may be investigated by probing with a thin instrument passed along the body adjacent to the porous surface before an attempt is made to withdraw the prosthesis.

Some prostheses, such as the one illustrated in FIG. 1, have a head integral with the body rather than being connected thereto by a self-holding taper. The ultrasonic transducer may be coupled to such a prosthesis by way of a threaded hole, or a spherical socket may be used to mate with the spherical head and provide good energy transfer.

An alternative technique may be employed for disrupting cancellous bone adjacent to the porous surface of the prosthesis. According to this technique an ultrasonic transducer 31 (FIG. 1) is threaded onto a conventional osteotome 32 and the osteotome is inserted along the porous ingrowth surface of the prosthesis 10 for disrupting a narrow channel of cancellous bone. By repeatedly inserting ultrasonically vibrating osteotomes along different areas of the body of the prosthesis, sufficient cancellous bone can be disrupted to free the prosthesis from the bone and permit its withdrawal with limited trauma to the patient. This technique for disrupting cancellous bone may be used in areas readily accessible at the proximal end of the prosthesis and ultrasonic vibration of the entire prosthesis may be employed for disrupting cancellous bone adjacent to the distal end of the prosthesis.

It should be noted that disruption of the bone occurs at the impedance mismatch between the metal and the bone. There is sufficiently low energy transfer through the bone and other tissues to avoid significant damage to the cancellous bone or cortex remote from the interface. Preferably the energy level is kept low enough that there is insignificant disruption of cortical bone in places where the shank of the prosthesis contacts such bone.

When removing a porous ingrowth prosthesis by ultrasonically vibrating osteotomes, equipment similar to that described in the Engelbrecht patent, supra, may be employed, the disclosure of which is hereby incorporated by this reference. Osteotome blades are available with male threaded ends for attachment to handles or the like. The threaded end makes a convenient place for coupling an ultrasonic transducer to the osteotome. The threaded tip of a transducer may be placed in the threaded hole 19 in a prosthesis as illustrated in FIG. 1 for efficiently coupling the ultrasonic vibrations between the transducer and the prosthesis. The way of coupling the transducer to the osteotome is not of significance and other means may be employed. Coupling to the self holding taper of a prosthesis is preferred.

It will also be noted that the power levels required when a transducer is coupled to an osteotome are considerably less than when a transducer is coupled to the prosthesis itself, since the area of the interface at which cancellous bone is being disrupted is considerably different.

A technique for removing a prosthesis by ultrasonically vibrating it may also be employed where the prosthesis has a substantially smooth surface and is secured in the bone by a cement such as polymethylmethacrylate (PMMA). In such an embodiment the PMMA remains softened and can be readily disrupted while ultrasonic vibrations are being applied. When vibrations are discontinued, the PMMA may become more rigid. It is, therefore, desirable when removing a prosthesis which is cemented in place, to apply ultrasonic vibrations and a withdrawing force simultaneously. This assures that a minimum withdrawal force is used for withdrawing the component. Again, if the prosthesis is not removed readily with a withdrawing force which may be steady or in the form of impact, the power level may be increased until a reasonable withdrawing force is sufficient for withdrawing the prosthesis from the medullary canal.

After removing the femoral stem 10, the revision procedure further requires the removal of the PMMA from the femoral canal. By energizing various specialized tool bits with ultrasonic energy, the tools easily slice through the softened PMMA and separate the PMMA from the adjacent cancellous bone 15. A variety of ultrasonic energy-activated tool bits or tips can be used during the cement removal procedure. For example, a gouge can be used to debulk cement from a proximal area, a flat osteotome can be used to separate the cement from the cancellous bone, a slitter or a hoe can be used to slice through the cement, and a cement plug modification tool, such as a plug removal tool bit 44 shown in FIG. 5, can be used to remove a cement plug at the distal end of the femoral canal.

Thus, there has been provided in accordance with another aspect of the present invention a mechanical junction for facilitating the rapid attachment and removal of any of the plurality of tool bits during the course of a surgical procedure. In addition to permitting rapid connection and disconnection within the sterile field, the junction of the present invention achieves a high, evenly distributed compressive force to optimize propagation of ultrasonic energy from the transducer to a tool bit, while maintaining a relatively small outside diameter of the ultrasonic tool.

Referring to FIG. 5, there is illustrated an ultrasonic medical tool 40 comprising an ultrasonic handpiece transducer 42 and an ultrasonic energy-activated tool bit 44 coupled to the handpiece transducer 42 via an extender 46. A first junction 43 is illustrated at the proximal end 48 of extender 46, and a second junction 45 is illustrated at the distal end 49 of extender 46. As used herein, the words proximal and distal refer to proximity to the handpiece transducer which supplies the ultrasonic energy to the tool bit.

Preferably, the location of each junction between the transducer 42 and tool bit 44 occurs at an antinode of the ultrasonic oscillation to minimize mechanical stress at the junctions. Thus, for example, junctions in an assembled tool will preferably be distanced apart by a whole number multiple of the distance λ/2, where λ equals the wavelength for a given frequency of ultrasonic oscillation. Preferably, the junctions will be located at multiples of λ/2±20% along the length of the assembled instrument. It should be noted that the junction(s) can occur at the nodes of oscillation so long as the junction is designed to withstand the increased mechanical stress at the nodal position. Due to the desirability of maintaining a relatively small tool diameter, however, together with efficient propagation, it is preferred that the junctions occur precisely at or approximately at antinodal positions.

For the cement removal process, it is desirable to employ a frequency in the range of from about 10,000 to about 100,000 Hz, preferably about 20,000 to about 60,000 Hz, and most preferably around 40,000 kHz. Thus, for example, in a most preferred embodiment of the present invention, detailed infra, antinodes are spaced approximately 2.4 inches apart in a 0.260 inch diameter extender comprising the preferred titanium alloy and operated at approximately 40 kHz. It is therefore understood that the dimensions disclosed below are exemplary for the specific tool and specific ultrasound frequency employed.

The length of the tool bit 44 and the length and number of extenders 46, discussed infra, is also influenced by its intended use. For example, when working inside the femoral canal, the length of the tool 44 together with the extender(s) 46 should allow the tool 44 to be appropriately positioned within the canal, but not so long as to impair the surgeon's ability to maneuver the tool. Generally, the depth of the femoral canal in a human adult is not greater than on the order of about 20 inches.

The length of the tool 44 is also influenced by the intended operating frequency for that particular tool. For most tools, maximum longitudinal oscillation at the distal end of the tool bit 44 is desirably obtained by positioning the tip to coincide with an antinode of the ultrasonic oscillation. Thus, as discussed above, the length of the tool 44 generally will equal a whole number multiple of λ/2 for the ultrasonic frequency employed and preferably will equal λ/2. For example, in a most preferred embodiment, for use in the cement removal procedure, the tool length will equal about 2.4 or 4.8 inches for operation at 40,000 Hz.

It is preferred that the outer diameter of each surgical component match the outer diameter of the component intended to be joined immediately adjacent thereto to eliminate surface irregularities. When working in environments where liquid such as blood or saline surrounds the tool, the transmitted ultrasonics can produce cavitations at projecting surfaces. Cavitation at areas other than the tool bit tip are undesirable because of the ultrasonic energy loss and because of the erosion effect on the surgical components. Thus, it is preferred that the outside diameters of the joined components be substantially identical at their interface so as to provide a substantially uniform external dimension through each junction.

The overall diameter of the tool bit 44 or extender 46 is limited only by the environment of its intended use. For example, in replacing the femoral component 10 of a hip joint replacement, the tool bit 44 diameter is limited by the interior diameter of the femoral canal which typically ranges between about 0.25 to about 0.75 inches. Preferably, the tool bit 44 diameter is sized even smaller to allow for the concurrent insertion into the femoral canal of additional apparatus such as irrigation and aspiration tubes, as well as a fiber optic visualization system.

The overall diameter also depends upon the configuration of the tool bit 44 tip. For example, a gouge may have a wider overall cross-sectional dimension than a slitter. In general, the diameter of the tool bit at the junction is less than about ½ inch and preferably less than about ⅜ inch. More preferably, the junction diameter is about 0.260 inches.

The diameter of the tool bit 44 along its axial length can be tailored to produce a desired longitudinal oscillation or stroke at a tool tip 51. As known in the art, by changing the diameter of the tool along its length, the amplitude of the oscillation will also change. Thus, by decreasing the tool diameter either gradually (i.e., in a Gaussian shape) or by stepped diameter, the amplitude can be adjusted to achieve a desired stroke at the tool tip 51.

Preferably, each tool bit is configured to function optimally or nominally optimally for its particular use. Decreasing the cross section of the tool increases the stroke, i.e., produces a positive gain in longitudinal oscillation. Moreover, where the tool includes stepped diameters, the location of the cross-sectional changes affect the degree of gain produced. The closer the location of the cross-sectional change to a node, the greater the gain realized. Thus, by controlling the change in cross section, the shape of the dimensional transition, and the location of the dimensional transition, a specific gain may be obtained to tailor the stroke of the tool for optimum performance.

Alternatively, the stroke of each tool bit is adjustable by controlling the power setting of the generator. For ergonomic reasons, however, it is preferred that each tool bit be tailored to operate nominally at its optimum without adjusting the generator power level.

In general, the stroke of the tool tip 51 (FIG. 5) should not be so great as to over stress the tool 44. For example, in a preferred embodiment of the present invention, with the diameter equal to 0.260 inches in a titanium alloy tool, the stroke is generally no more than about 0.004 inches peak-to-peak. It is understood, however, that the shape of the tool or the tempering of the material comprising the tool can increase its ability to withstand greater stress at larger strokes. But it has been found that stroke lengths greater than about 0.008 inches peak-to-peak do not appreciably increase the effectiveness of the tool to remove cement or fashion the cancellous bone, at 40 kHz frequency.

More preferably, the longitudinal profile of the tool should be designed to produce a stroke length of from about 0.001 inches to about 0.004 inches, and most preferably a stroke length of about 0.002 inches for the majority of tool tip 51 configurations. For tool tips with relatively large surface area, the stroke is preferably larger, such as in the range of 0.002 to 0.004 inches peak-to-peak.

Preferably, the tool bits illustrated herein generally maintain a minimized thermal footprint. In other words, the tool bits are configured to minimize the frontal and side contact areas between the tool and the cement by including drafts or reliefs within the tool bit body. As a result, the ultrasonic energy concentrates at the working surfaces of the tool to optimize the performance of the tool. Energy dissipation by incidental contact with cement or tissue adjacent the surgical site is minimized.

Moreover, the tool bit configurations preferably minimizes the incidental dissipation of heat to adjacent tissue. The change of impedance at the interface surfaces between the tool bit and living tissue generates heat. The increased tissue temperature potentially increases the likelihood of denaturing protein in tissue and can produce localized necroses. Desirably, the configuration of the tool bits shown herein tend to reduce, if not eliminate, incidental contact with surrounding tissue, including cancellous bone.

Referring to FIG. 5, the illustrated tool bit 44 comprises a barb tip tool bit having a generally radially symmetrical body portion 70, which, preferably, is substantially cylindrical. A generally arrow-shaped opposing pair of projections 72 are positioned at the distal end of the tool bit 44 which ramp radially inwardly in the distal direction to form a sharp point. Preferably, the tool bit 44 additionally includes a second opposing pair of arrow-shaped projections 74 disposed on the proximal side of the first projections 72. The tool bit 44 additionally preferably comprises a substantially radially symmetrical distal portion 76 of reduced exterior dimension positioned between the projections 74 and the cylindrical body portion 70 to amplify the ultrasonic oscillations at the distal end of the tool bit, as known in the art and discussed above.

In use, the plug removal tool bit illustrated in FIG. 5 is inserted under ultrasonic energy into the cement plug which remains in the bottom of the femoral canal following removal of a cemented prosthesis. Softened cement flows up over the ramped surfaces and behind the barb of the energized tip, where it resolidifies upon interruption of power to the transducer. The tool may thereafter be manually retracted to pull the cement plug loose from the femoral canal.

Figure 14:
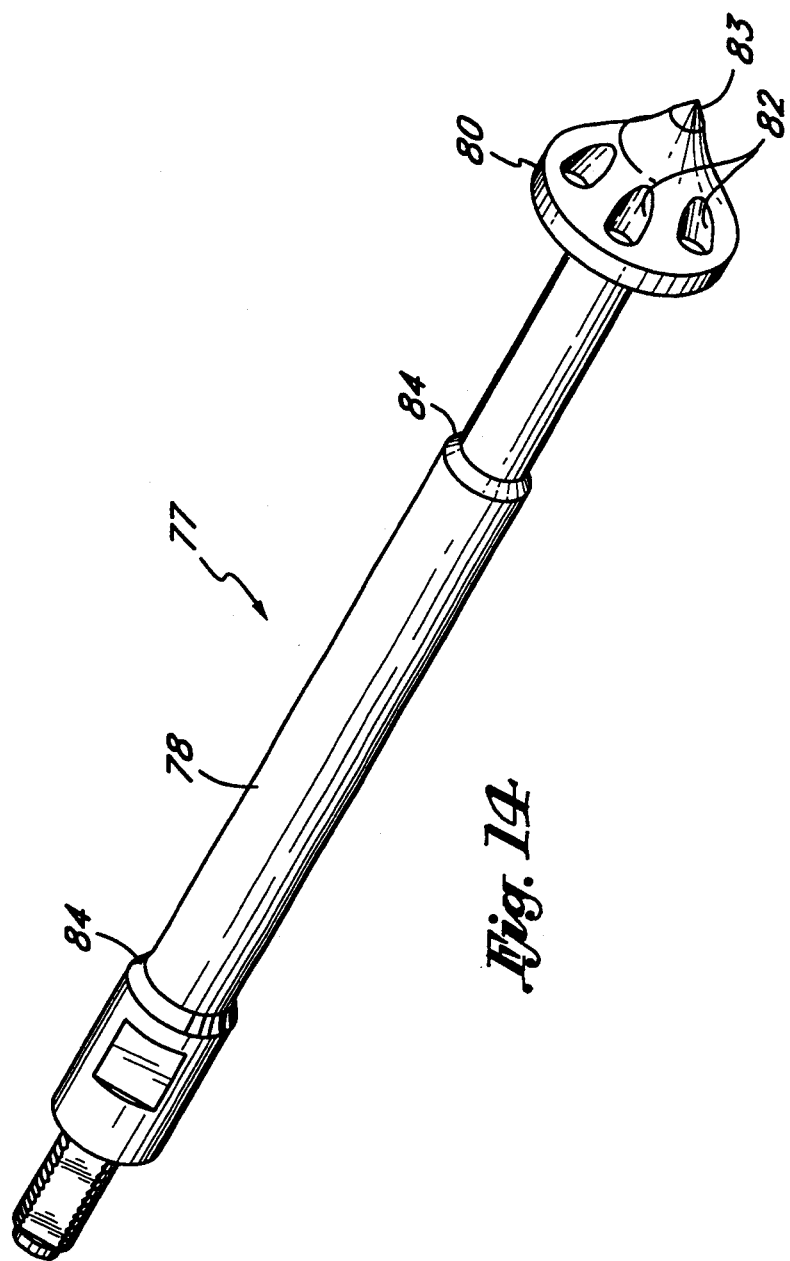
FIG. 14 is a perspective view of a disk drill tool tip.
Figure 15:
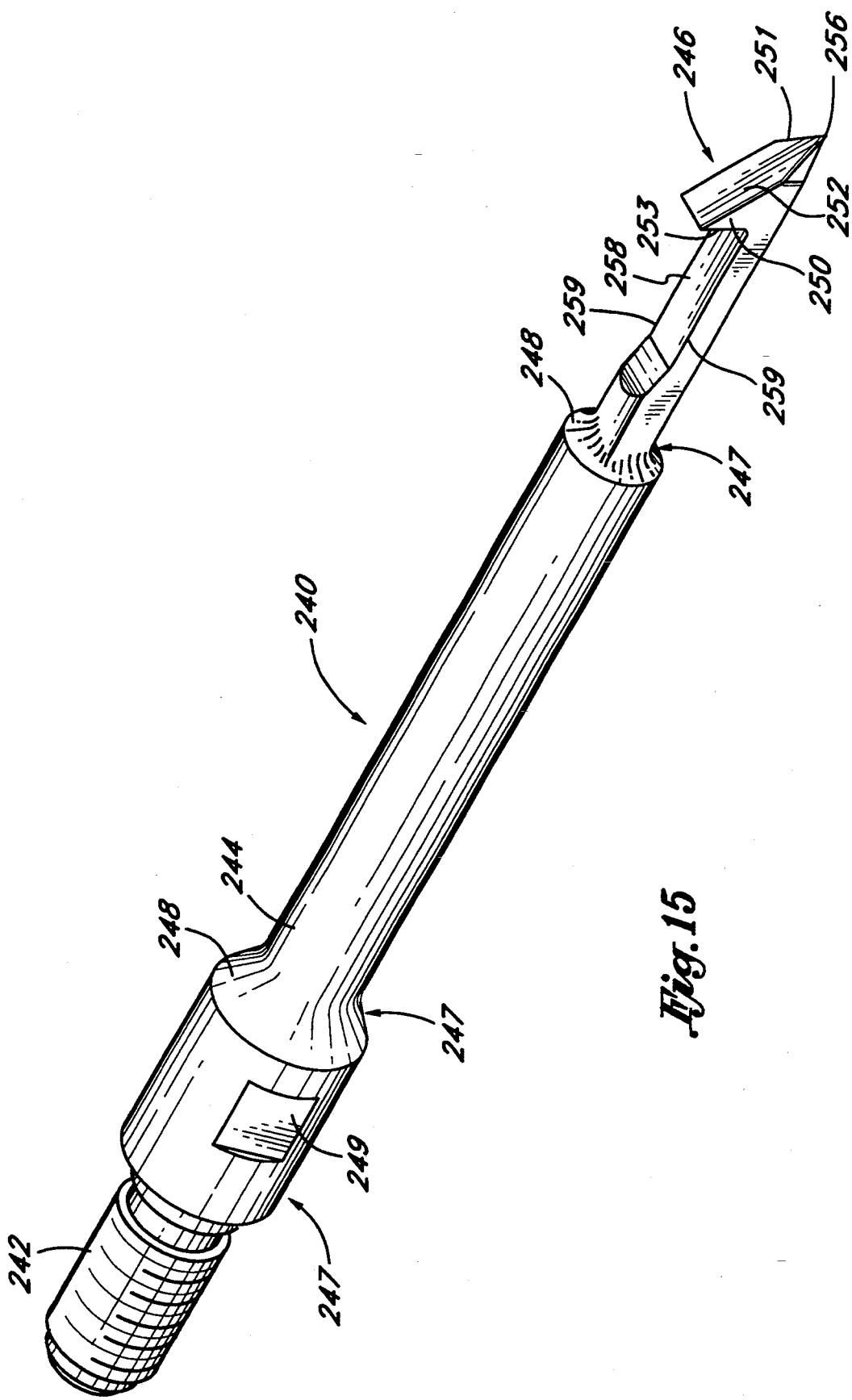
FIG. 15 is a perspective view of a barb tool bit in accordance with the present invention.

Although FIG. 5 illustrated the tool bit 44 as being a barb tip tool bit, it is understood that other tool configurations, such as a gouge, slitter or hoe, can be used as well. For example, FIG. 14 illustrates a Poly Methyl Methacrylate modification tool 77. The disk drill tool bit 77 comprises an elongate body portion 78 and a radially outwardly extending annular flange 80 positioned at the distal end of the tool bit 77. The flange 80 is provided with a plurality of apertures 82 extending therethrough in the longitudinal direction. Preferably, the annular flange 80 is inclined radially inwardly in the distal direction to produce a substantially cone shaped working tip 83.

In use, the conical tip 83 is embedded in the cement plug under ultrasonic energy with some softened cement extruding through the apertures 82. The tool is mechanically withdrawn from the canal to extract the cement extruded through the apparatus. Preferably, the apertures 82 are sized and positioned to optimize the extraction of the cement, while at the same time retaining sufficient structural integrity to withstand the combination of ultrasonic energy and physical manipulation by the clinician. Generally, the tool comprises from about 4 to about 20 apertures 82 evenly spaced about the circumference of the conical tip 80. Preferably, about six to about ten apertures are provided.

It is also preferred that the body 78 have one or more diameter reductions 84 to amplify the ultrasonic oscillations at the distal end of the tool, as discussed above.

The design of the tool bits described herein is preferably influenced by five basic design parameters to produce an optimally performing tool bit. First, the tool bits are tailored to produce a desired gain for the particular function of the tool bit in accordance with the discussion supra. Advantageously, each tool bit is designed to stroke at optimum oscillation for a set level of power. As a result, a surgeon can interchange tool bits without having to reset the power level of ultrasonic transducer every time he or she switches tool bits. Such optimization can be accomplished by routine experimentation by one of skill in the art, based upon the teachings herein.

Second, the configurations of the tool are also chosen to efficiently distribute mechanical stress throughout the tool bit and the tools are sized to provide adequate mechanical strength. Third, the configuration of each tool bit reflects the particular function performed by the tool. Fourth, the size of the tool bits are generally dictated by the environment of use, and preferably the dimensions are significantly smaller than the intended environment to permit the concurrent insertion of aspiration, irrigation and visualization equipment into the surgical site. Finally, the material of the tool bit is selected to efficiently propagate the ultrasonic energy, to be biologically compatible and to provide sufficient mechanical strength.

In addition, each tool bit, oscillating at approximately 40 kHz, provides the surgeon with both tactile and audio feedback indicating when the surgeon is cutting into cortical bone. The stokes of each tool bit have been selected to efficiently cut PMMA cement and/or cancellous bone, but resist cutting cortical bone. When the tool bits contact cortical bone, the oscillation of the tool bit against the cortical bone produces a high pitch sound, audibly indicating the contact. Consequently, the surgeon can sense both audibly and tactily the position of the tool bit relative to the surround tissue.

Although FIGS. 15 through 45 illustrate the tools as including a threaded male connector to facilitate coupling with an ultrasound transducer or waveguide (i.e., extender), it is understood that alternative connector designs, such as, for example, the spline/key-way connectors shown in FIGS. 7-13 and discussed below, may be used as well. In addition, although the preferred use of the tool bits disclosed below is in connection with cement removal from the acetabulum and femur, it is contemplated that these tool may be used equally well in connection with cement modification associated with other procedures relating, for example, to knees, shoulders, wrists, elbows and fingers.

FIGS. 15-20 illustrate a barb tool bit 240 used to extract cement plugs anchoring an acetabular component into the acetabulum. The barb tool bit 240 comprises a connector 242, an elongated, cylindrical shank 244, and a barb 246.

The elongated, cylindrical shank 244 preferably includes at least one step concentrator 247 (i.e., a step in its diameter) to tailor the gain of the barb tool bit 240 to function optimally; i.e., to preferably stroke at approximately 0.001 to 0.004 inch, peak to peak, and more preferably at about 0.0015 inch, peak to peak at 40 kHz. Because the barb tool bit 240 only requires a gain sufficient to produce a stroke of about 0.002 inch, the step concentrator 247 can be located closer to antinodes to reduce the stress at the location of the step and to reduce the overall gain of the tool bit 240. In addition, the longitudinal profile as illustrated in FIGS. 16–18, is preferably designed to improve visualization, irrigation and aspiration by decreasing the diameter of the tool along its length. The reduced cross-section further allows the barb tool bit 240 to insert into tighter areas. Fillets 248 blend together the diameter steps 247 to improve the mechanical strength of the tool bit 240 at the transition locations.

In a most preferred embodiment, the shank 244 has a diameter at a proximal end 247 equal to about 0.260 inch and steps down to a diameter of approximately 0.150 inch on the distal side of the wrenching flats. Proximate to a distal end 251 of the barb tool bit 240, the shank 244 preferably includes a second step 247 in diameter down to approximately a 0.100 diameter.

The barb 246 comprises a generally half arrowhead-shaped projection 250 extending radially and having a surface 252 ramping radially outwardly in the proximal direction from the distal end 251 of the barb tool bit 240. The angle between the ramped surface 252 and the tool longitudinal axis facilitates the penetration of the barb 246 into the cement and provides enough area on surface 253 on the proximal side of the barb 246 to leverage the cement plug out of the pocket. Preferably, the angle ranges between 20° and 75°, more preferably ranges between 30° and 60°, and most preferably equals 45°.

The barb 246 attaches to the distal end of the shank 244, with a fillet 254 improving the strength of the juncture to compensate for the torque applied on the barb 246 during use, as will be discussed below. At the distal end 251, the barb 246 includes a sharp tip 256 to ease insertion of the barb 246 into the cement. In other words, the sharpened tip 256 allows the surgeon to mechanically position the tool bit tip at a precise location before ultrasonically energizing the bit 240. This prevents the distal end 251 of the bit 240 from skating over the surface 253 of the cement or cancellous bone.

The barb 246 preferably has a size easily insertable into small pockets of cement. The greatest cross-sectional dimension of the barb 246, in a plane transverse to the axis of the shank 244, is generally less than about 10 mm, more preferably between 2 and 6 mm, and most preferably equal to approximately 4 mm (0.150 inch). The width of the barb 246, however, should not be so small as to strip out by itself, i.e., not have enough leverage area on surface 253 on the proximal side of the barb. It is also preferred that the barb 246 has a limited length, measured along the longitudinal axis of the tool from the leverage surface to the tip 256, so that the barb 246 can be inserted into shallow pockets of cement.

On the proximal side of the barb 246, the shank preferably includes a recess 258 to receive cement flowing behind the barb 246 during use. The recess 258 also improves the leverage of the barb 246 as more cement flows behind the barb 246 and the shape edges 259 of the recess 258 tend to resist rotation of the tool bit 240 in solidified cement.

The surgeon uses the barb tool bit 240 after removing the acetabular component with the acetabular tool bit 200 and after removing the cement lining the acetabulum in the pelvic bone with a combination of gouges, scoops and osteotomes. The barb 246 facilitates removal of small pockets of cement used to anchor the acetabular component into the pelvic bone. The surgeon, with the aid of the ultrasonics, forces the barb 246 into the pocket of cement to a point completely embedding the entire barb 246. With the barb tool bit 240 still ultrasonically energized, the surgeon rotates the barb through an angle, such as 90°, to position virgin cement on the proximal side of the barb 246. After de-energizing and letting the cement cool for approximately 10 to 15 seconds, the surgeon manually (i.e., without ultrasonics) extracts the cement out of the pocket by retracting the barb tool bit 240.

Having removed the femoral cement cylinder mantle, the surgeon removes a cement or polyethylene plug at the distal end of the femoral canal. The surgeon may use any of the following tools and procedures to remove such plug.

FIGS. 21–25 illustrate a plug puller 480 comprising a connector 481, a shank 482 and a barbed tip 483. The elongated, cylindrical shank 482 preferably includes a step concentrator 484 (i.e., a step in its diameter) to tailor the gain of the barbed tool bit 480 to function optimally; i.e., to preferably stroke at approximately 0.001 to 0.004 inch, peak to peak, and more preferably at about 0.0015 inch, peak to peak at 40 kHz. The larger the transverse cross-sectional size of the barbed tip 483, the more gain needed for a fixed level power setting of the driving unit. In the most preferred embodiment, in which the barbed tip 483 has a transverse width of approximately 0.260 inch, it is preferred that the stepped concentrator 484 be located proximate to an antinode to minimize the gain realized and to reduce the mechanical stress at the conical concentrator 484.

In a most preferred embodiment, the shank 482 has a diameter at a proximal end 485 equal to about 0.260 inch and steps down to a diameter equal to about 0.150. Advantageously, the conical concentrator 484 includes a fillet 486 forming a transition between the smaller diameter and the cone to improve the mechanical strength of the shank 482, as known in the art.

The barbed tip 483 includes a generally arrow-shaped opposing pair of projections 487 positioned proximate to a distal end 488 of the barbed tip 483. The projections 487 ramp radially inwardly in the distal direction to converge into a sharp point 489 at the distal end 488 of the barbed tip 483. Preferably, an angle formed between a ramp surface 490 of the projection 487 and the longitudinal axis of the plug puller 480 is less than 45°, and more preferably is equal to about 30°.

The transverse width of each projection 487 has sufficient size to define a sufficiently large leverage surface 491 to facilitate the removal of the cement plug. The transverse width of the barbed tip 483, however, is preferably as small as possible to facilitate insertion into the narrow distal end of the femoral canal.

Preferably, the barbed tip 483 additionally includes a second opposing pair of arrow-shaped projections 492 disposed on the proximate side of the first pair of projections 487. The second pair of projections are preferably positioned at a sufficient distance from the leverage surfaces 491 of the first pair of projection 487 to prevent the barbed tip 483 from stripping out of the cement when retracted.

The barbed tip 483 includes the sharp point 489 at the distal end 488 to ease insertion of the plug puller 480 into the cement plug. In other words, the sharpened tip 489 allows the surgeon to mechanically position the tool bit tip 489 at a precise location before ultrasonically energizing the bit 480.

As illustrated in FIG. 21, the pairs of projections 487, 492 are positioned along a shaft 493 which extends from the tip 489 in the proximal direction along an axis generally aligned with the longitudinal of the shank 482. The shaft 493 preferably has a diameter sufficiently sized to provide adequate mechanical strength and to minimize the thermal footprint of the barbed tip 483 (i.e., the surface area of the tool in contact with the cement). In addition, the shaft 493 may have a smaller diameter than the shank 482 to increase the gain at the distal end of the tool in a manner similar to a stepped concentrator, as previously described.

On the proximal side of the projections 487, 492, the shaft includes fillets 494 to improve the mechanical strength of juncture between the projections 487, 492 and the shaft 493, as known in the art.

The barbed tip 483 preferably additionally includes a generally circular disk 495 circumscribing the distal end of the shank 482 and positioned between the distal end of the shank 482 and the shaft 493. The disk 495 provides the surgeon with tactile feel to indicate when the barb projections 487,492 have fully been inserted into the cement plug. Preferably, the disk 495 includes a pair of longitudinal notches 496 disposed at the circumferential edge of the disk 495 to provide pressure relief for fluid or cement on the distal side of the disk 495.

The surgeon, with the aid of ultrasonics, forces the barbed tip 483 into the cement plug positioned at the distal end of the femoral canal to a point completely embedding the barbed projections 487, 492. The surgeon can sense when the barbs 487, 492 have fully inserted as the disk 495 contacts on the plug. Where the disk 495 has a cross-sectional dimension generally equaling the diameter of the distal end of the femoral canal, fluid and cement on the distal side of the disk flow through the notches 496 to relieve the pressure on the distal side of the disk 495.

With the plug puller 480 still ultrasonically energized, the surgeon rotates plug puller 480 through an angle, such as 90°, to position virgin cement on the proximal side of the projections 487, 492. After de-energizing and letting the cement cool for approximately 10 to 15 seconds, the surgeon manually (i.e., without ultrasonics) extracts the cement plug out of the canal with the use of a slide hammer or like tool coupled to the proximal end 485 of the plug puller 480.

FIGS. 26–30 illustrates another embodiment of a disk drill 500, designed to extract cement from the cement plug located at the distal end of the femoral canal. The disk drill 500 comprises, a connector 501, an elongated shank 502, and a generally conical tip 503. The elongated, cylindrical shank 502 preferably includes at least one stepped concentrator 504 (i.e., a pronounced step in its diameter) to tailor the gain of the tool bit 500 to function optimally; i.e., to preferably stroke at approximately 0.001 to 0.004 inch, peak to peak, and more preferably at about 0.0015 inch, peak to peak at 40 kHz. The larger the size of the disk 503, the more gain needed for a fixed level power setting of the driving unit.

In one preferred embodiment, where the conical tip 503 has a diameter of about 0.500 inch, it is preferred that the stepped diameter 504 occur close to a node to increase the amount of gain achieved by the stepped configuration. In another preferred embodiment, the conical tip 503 has a diameter of approximately 0.375 inch and the step in the shank diameter occurs close to an antinode because this tool demands less gain to produce the desired stroke. The overall diameter of the conical tip 503 is limited by the diameter of the femoral canal proximate to the cement plug.

In a most preferred embodiment, the shank 502 has a diameter at the proximal end equal to about 0.260 inch and steps down to a diameter ranging between 0.075 and 0.150, and more preferably between approximately 0.100 and 0.125 inch. Advantageously, the shank 502 includes a fillet 505 forming a transition between the stepped diameters to improve the mechanical strength of the shank 502, as known in the art.

The length of the tool bit 500 also varies to tailor the gain of the tool bit 500 and tunes the tool bit for the same frequency as the rest of the tool bits.

The conical tip 503 connects to the distal end of the shank 502, as illustrated in FIG. 26. The conical tip 503 tapers distally from a base 506 to a vertex 507. Preferably, as shown in FIG. 26, a surface 509 of the tip 503 has an arcuate taper from the base 506 to the vertex 507, with the arcuate taper having a radius of curvature.

A fillet 510 smoothly joins the surface of the shank 502 distal end with the base 506 proximal side.

The conical tip 503 includes a plurality of apertures 511 piercing through the tip base 506, the axis of each aperture 511 being generally parallel to the longitudinal axis of the tool. Although FIGS. 26 and 30 illustrate the apertures 511 as having a circular configuration, it is understood that other aperture configurations, such as, for example, a truncated conical section shape or a trapezoidal section shape, may be used as well. Preferably, the apertures 511 are sized and spaced about the conical tip 503 to minimize the surface area on the distal side 512 of the conical tip 503 without sacrificing the structural strength of the webbing 514 between each aperture 511 and the shank 502. More preferably, the apertures 511 are evenly spaced around a radius of the conical tip 503, maintaining approximately 0.030 inch between each aperture edge 513, between each aperture edge 513 and the circumferential edge of the conical tip 514, and between each aperture edge 513 and the diameter of the shank 502, as illustrated in FIG. 30. The number of apertures 511, therefore, preferably depends upon the diameter of the conical tip 503 and the above recited design requirements.

In one preferred embodiment, the conical tip 503 has a diameter of 0.500 inch, a shank 502 diameter proximate to the conical tip 503 equal to 0.125 inch, and five 0.125 inch diameter holes 511 spaced evenly about a 0.362 diameter circle, each spaced apart by 72°. In another preferred embodiment, the conical tip 503 has a diameter of 0.280 inch, a shank 502 diameter proximate to the conical tip 503 equal to 0.100 inch, and six 0.055 inch diameter holes 511 evenly spaced 60° apart about a 0.187 diameter circle. In a further preferred embodiment, the conical tip 503 has a diameter of 0.375 inch, a shank 502 diameter proximate to the conical tip 503 equal to 0.125 inch, and seven 0.067 inch diameter holes evenly spaced 51° apart about a 0.248 inch circle.

In use, the vertex 507 contacts a cement plug and melts the PMMA material immediately. Further travel in the distal direction causes the cement to flow around the tapered nose of the disk drill 500 and through the holes 511. Slight rocking rotation of the tool improves its effectiveness. Preferably, the tool is advanced distally for about an inch and then retracted from the femoral canal. The surgeon subsequently wipes off the extruded PMMA and repeats the process. A surgeon may also use the disk drill 500 to remove cement from the sides of the canal, especially when debulking, in either the normal proximal to distal direction or in the distal to proximal direction.

Figure 31:
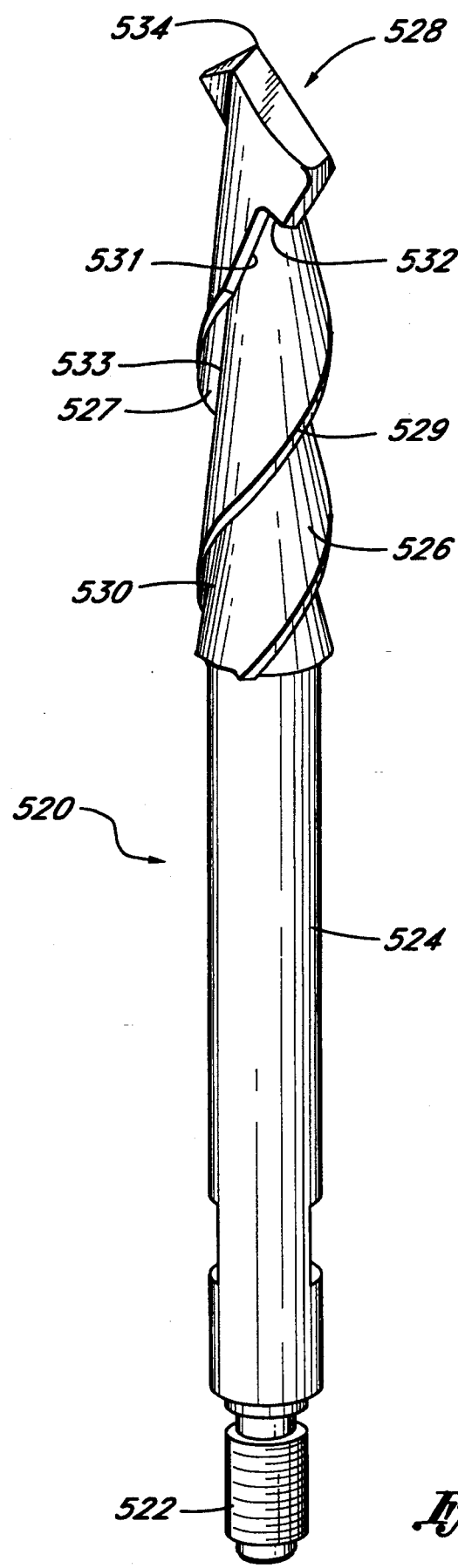
FIG. 31 is a perspective view of a push drill of the present invention.
Figure 32:
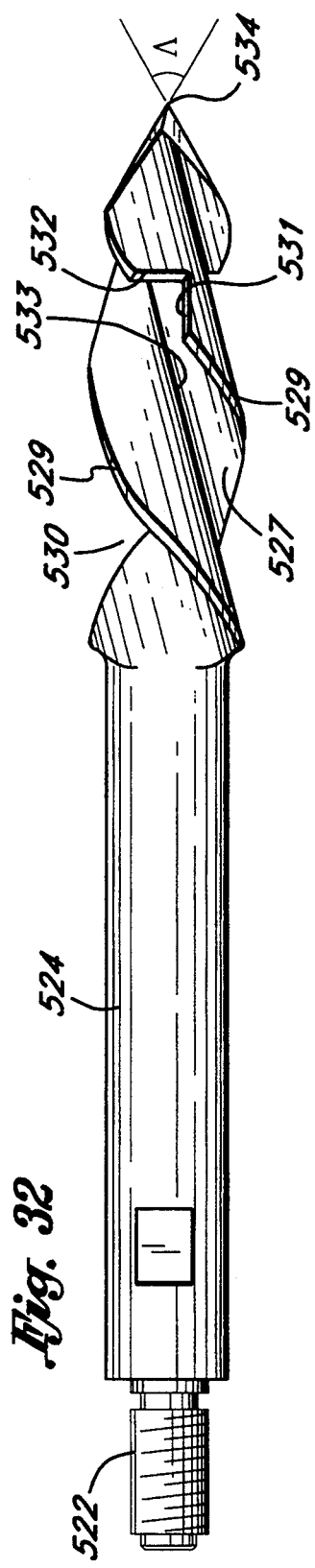
FIG. 32 is a plan view of the push drill of FIG. 31.
Figure 33:
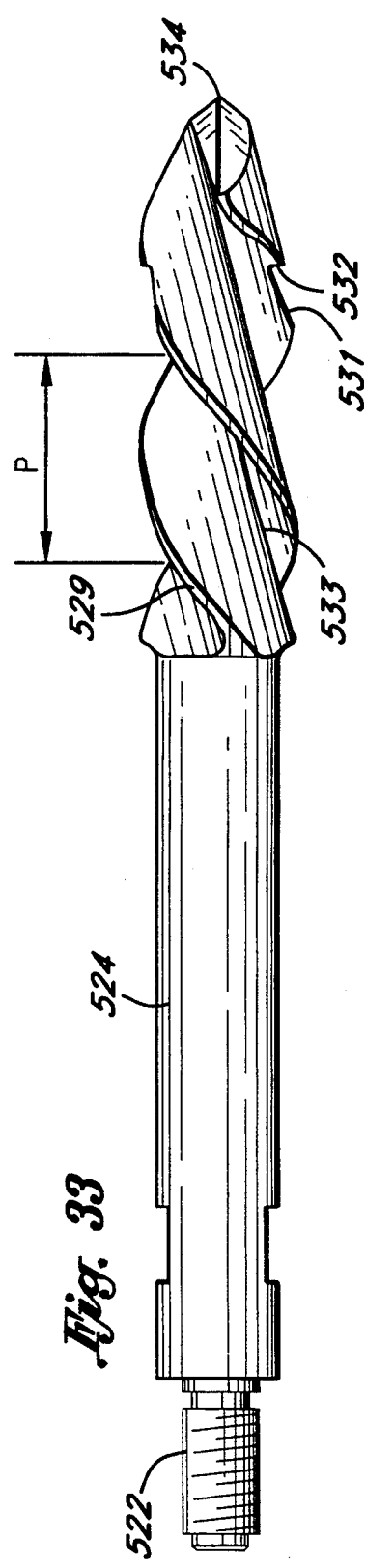
FIG. 33 is a side view of the push drill of FIG. 31.
Figure 34:
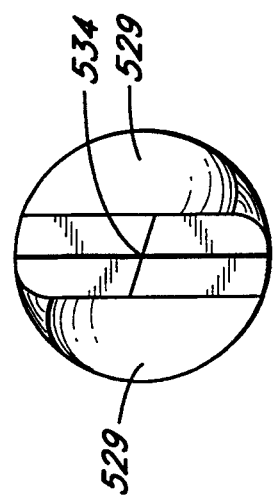
FIG. 34 is a left end view of the push drill of FIG. 33.
Figure 35:
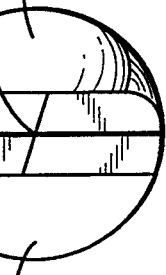
FIG. 35 is a right end view of the push drill of FIG. 33.

A push drill 520, as illustrated in FIGS. 31–35 offers the surgeon the ability to use a single tool bit either as a plug puller or as a plug drill. FIG. 31 illustrates the push drill 520 comprising a connector 522, an elongated, cylindrical shank 524 and a drill tip 526.

Referring to FIG. 31, the drill tip 526 is formed on the distal end of the shank 524. The drill tip 526 has a parabolic flute 527 spiraling from a distal end 528 about the longitudinal axis of the push drill 520 in the proximal direction. The flute 527 has a length less than the length of a standard cement plug and preferably as short as possible to enable the direction of travel of the drill tip to change while drilling, as would be necessary when used with a cement plug having a curvature along its length. In the most preferred embodiment, the flute 527 has a length equal to about 1.00 inch.

The flute 527 has a sufficiently large rake angle (i.e., a helix angle) to permit pushing the drill tip 526 into the cement plug with a force of about 2 to 10 pounds applied in the distal direction. The rake angle preferably ranges between 20° and 70°, and more preferably ranges between 30° and 60°. Within the preferred range of rake angles, it is further preferred that the flute 527 have a pitch P measured from the center line of one land 529 (i.e., the periphery portion of the drill body between the flute 527) to the center line of an adjacent land 529 (as shown in FIG. 95) within the range of from about 0.20 to 0.75 inch, and more preferably equal to about 0.45 inch.

The drill tip 526 has a transverse cross sectional dimension sized smaller than the interior diameter of the distal end of the femoral canal adjacent to the plug. Preferably, the drill tip 526 diameter is less than 1.00 inch, and more preferably equals either 0.750, 0.625, 0.500, 0.375, or 0.250 inch; the cross-sectional dimension being selected depending on the cross section dimension of the plug and the amount of cement that the surgeon wants to remove.

The drill tip 526 preferably includes a second parabolic flute 530 positioned about the longitudinal axis of the push drill 520 diametrically opposite the first parabolic flute 527. In the most preferred embodiment, the distance between a land 527 formed between the first flute 527 and second flute 530 and an adjacent land 527, likewise formed between the first flute 527 and the second flute 530, is equal to about 0.45 inch.

The drill tip 526 includes a pair of diametrically opposed notches 531 formed in the lands 529 on opposite sides of the drill tip 526. Each notch 531 generally has a "V" shape with a distal edge 532 cut generally perpendicular to a tangent of the land 529, as illustrated in FIG. 94. As a result, when the surgeon manually retracts (i.e., without ultrasonics) the push drill 520, the cement in the notch 531 behind the distal edge 532 squarely abuts against the distal edge 532 to improve the holding power of the drill tip 526 in the cement plug. The notch 531 preferably extends across the land 529 towards the axis of the drill tip 526 to a point adjacent a web 533 (i.e., the central portion of the drill tip 526 that joins the ends of the lands 529), to maximize the surface area of the distal edge 532.

The notches 531 are positioned on the drill tip 526 as close to the distal end 538 as possible to minimize the depth to which the drill tip 526 needs to be embedded for pulling out the cement plug, without significantly weakening the distal end 528 of the drill tip 526. Preferably, the notches 531 are located at least 0.125 inch from the distal end 528 of the drill tip 526 on its proximal side.

The push drill 528 includes a sharp tip 534 disposed at its distal end 528 defining a point angle Λ. Preferably, the point angle is sufficiently large to give the distal end 528 of the push drill 520 a low angle of attack to permit the surgeon to easily push the drill tip 526 through the cement plug. Preferably, the point angle Λ is larger than 45° and more preferably equal to about 60°.

In the most preferred embodiment, the shank 524 has a uniform cross sectional dimension equal to about 0.260 inch and a length of about 1.50 inch. The drill tip 526 has a cross-sectional area less than the shank 524, and thus the reduction in cross section produces a gain. Preferably, the drill tip 526 strokes at about 0.001 to 0.003 inch, and more preferably at about 0.0015 inch for a small cross sectional dimension drill tip 526 (e.g., 0.250 inch) and about 0.002 inch for a larger cross sectional dimension drill tip 526 (e.g., 0.750 inch).

In use, the surgeon forces the energized push drill 520 into the cement plug by applying a force of preferably about 5 pounds in the distal direction. As the distal end 528 of the drill tip 526 passes through the cement, the cement flows through the flutes 527, 530 and into the notches 531. The surgeon preferably embeds the drill tip 526 in the cement plug to a depth of about 0.50 inch.

When using the push drill 520 as a plug puller, the surgeon de-energizes the tool bit and waits approximately 10 seconds for the cement to solidify around the drill tip 526. The surgeon can subsequently extract the plug by using a slide hammer coupled to the proximal end of the push drill 520, as known in the art.

The surgeon may also use the push drill 520 to bore through the cement plug to produce a cement cylinder removable with the tools and procedures discussed supra. After embedding the drill tip 526 to a depth of about 0.50 inch, the surgeon de-energizes the push drill 420 and waits for about 5 seconds. The surgeon subsequently rotates the push drill 520 to break off the distal end of the cement helicals contained in the flutes 527, 530 of the drill tip 526 and retracts the push drill 520 in the proximal direction. The surgeon then wipes off the cement helicals from the drill tip 526 and repeats the procedure as required.

FIGS. 36–40 illustrates a trephine 540 comprising a connector 541, an elongated cylindrical shank 542, and a generally tubular head 543 having an opening 544 at its distal end.

Figure 36:
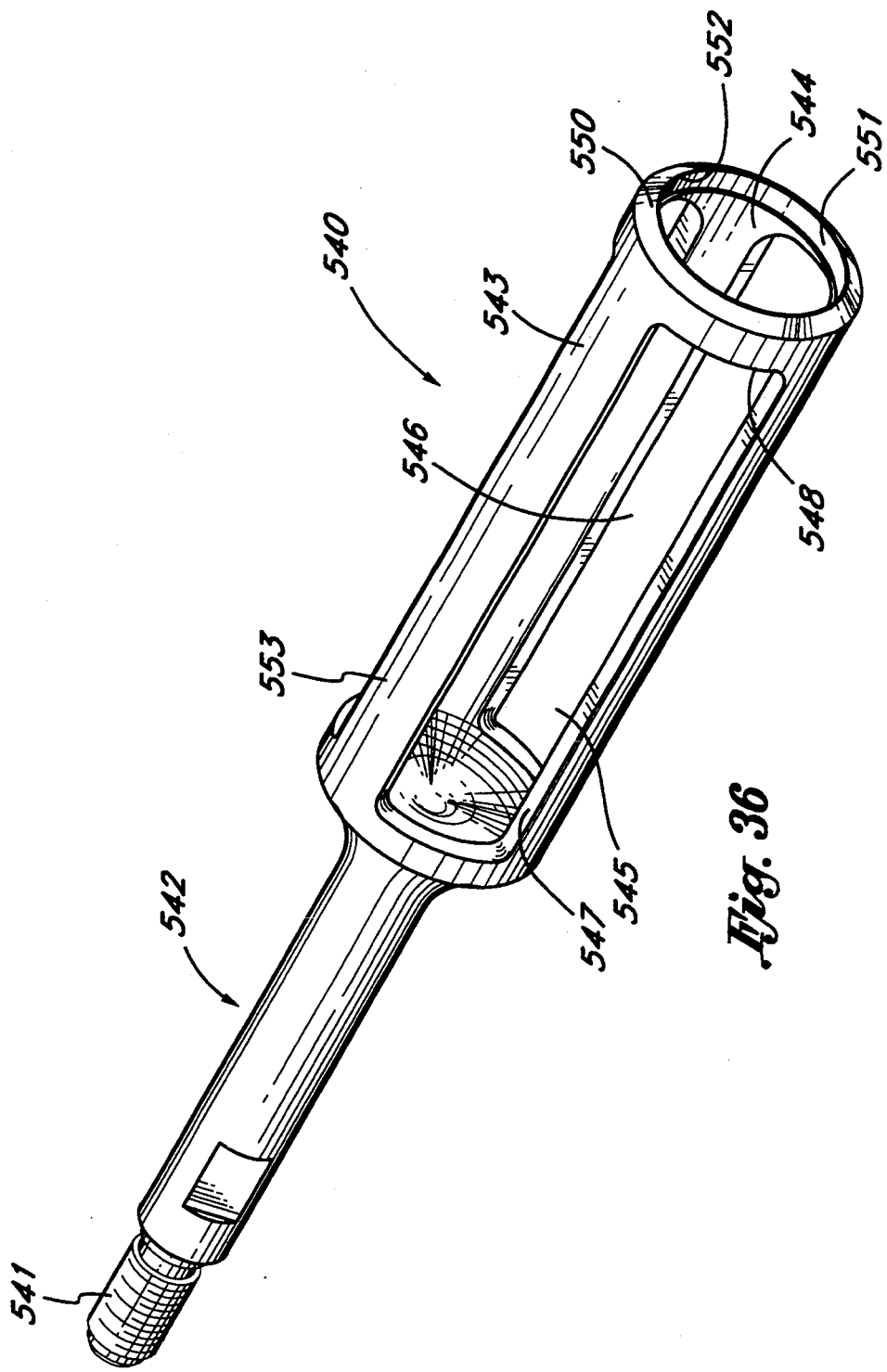
FIG. 36 is a perspective view of a trephine of the present invention.

As shown in FIG. 36, the shank 542 diverges radially outwardly into the hollow head 543. Preferably, the outer diameter of the head 543 has a size commensurate with the diameter of the distal end of the femoral canal.

The head 543 includes at least one generally rectangular window 545 opening into an interior cavity 546 of the head 543. The trephine 540 as shown in FIG. 93, preferably has three rectangular windows 545 to maximize visualization into the interior cavity of the head 543 during use. It is contemplated, however, that virtually any number and/or configuration of windows 545 can be used with lesser visualization.

Preferably, the windows 545 are symmetrically spaced about the circumference of the head 543 to ensure symmetrical propagation of ultrasound along the longitudinal axis of the tool.

For manufacturability purposes, the windows 543 may include a chamfer along edges 547 of the windows 543. An edge 548 on the distal side of the window 545, however, preferably is perpendicular to the longitudinal axis of the tool to form an abutment surface 549 between the cement and the tool thus providing leverage on the cement when retracting the tool to pull the cement out with the tool. The windows 545 provide a vent for the cement pushed into the tubular head 543 during use and facilitate the removal of the cement from the tubular head 543.

The walls of the tubular head 543 have a thickness, measured in the transverse direction, sufficient to resist flexure and withstand the stresses produced by the propagating ultrasound energy. At its distal end, the head 543 includes a chamfer 550 circumscribing an opening 544 and a counterbore 551 to form a sharp edge 552 at the distal end of the tool for knifing into a cement plug.

Although the transverse dimension of the trephine 540 increases distally, the cross-sectional area of the tool decreases to produce a desired ultrasonic gain. The position at which the shank 542 diverges into the head 543 is located proximate to a node to produce the desired gain.

The length of the head 543 is preferably dictated by the length of a nominal plug and the mechanical structural limitations imposed on struts 553 between the windows 545.

The surgeon uses the trephine 545 to core out the cement plug to form a cylinder which is subsequently removed with the other tool bits and procedures described above. The trephine 540 also allows the surgeon to work on the cement plug with a portion of another tool embedded in the plug, as would be the case, for example, if the plug puller 480 or disk drill 500 broke during use.

Figure 41:
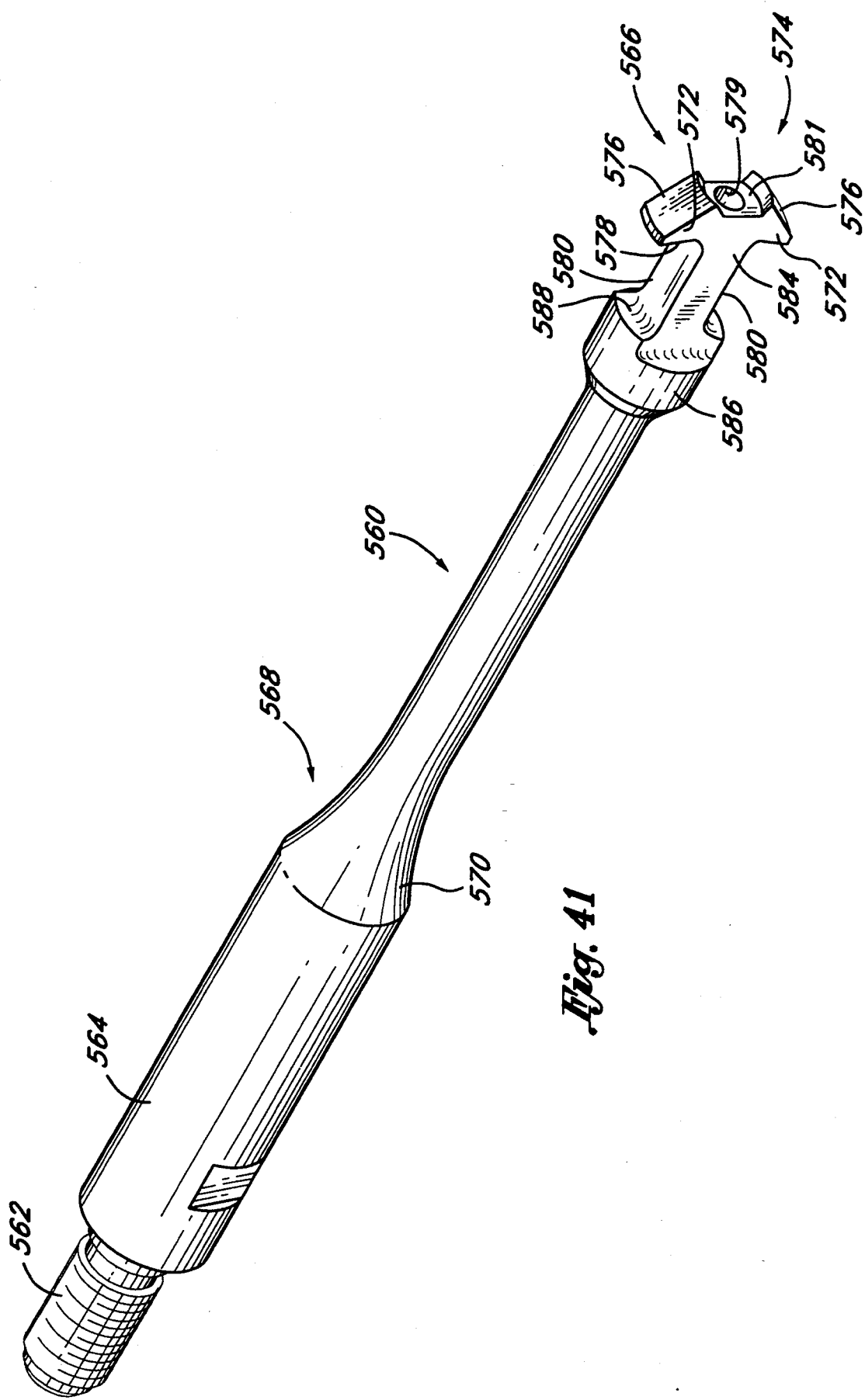
FIG. 41 is a perspective view of a poly-plug puller tool bit of the present invention.

FIGS. 41-48 illustrate a poly-plug puller 560 used to extract a polyethylene plug 561 (see FIGS. 46-48) of the type used to occlude the distal end of the femoral canal. As shown in FIG. 41, the poly-plug puller comprises a connector 562, a shank 564 and a barbed tip 566.

The elongated, cylindrical shank 564 preferably includes a conical concentrator 568 (i.e., a conical shaped change in its diameter) to tailor the gain of the poly-plug puller 560 to function optimally; i.e., to preferably stroke at approximately 0.001 to 0.004 inch, peak to peak, and more preferably at about 0.0015 inch, peak to peak at 40 kHz. In the most preferred embodiment, the conical concentrator 568 is located proximate to an antinode with the shank decreasing in cross section from 0.260 inch to 0.150 inch to minimize the gain realized and to reduce the mechanical stress at the conical concentrator 568. Advantageously, the conical concentrator 568 includes a fillet 570 forming a transition between the stepped diameters to improve the mechanical strength of the shank 564, as known in the art.

Referring to FIG. 42, the barbed tip 566 includes a generally arrow-shaped opposing pair of projections 572 positioned proximate to a distal end 574 of the barbed tip 566. The projections 572 ramp radially inwardly in the distal direction. Preferably, an angle formed between a ramp surface 576 of the projection 572 and the longitudinal axis of the poly-plug puller 560 is less than 60°, and more preferably is equal to about 45°.

Figure 48:
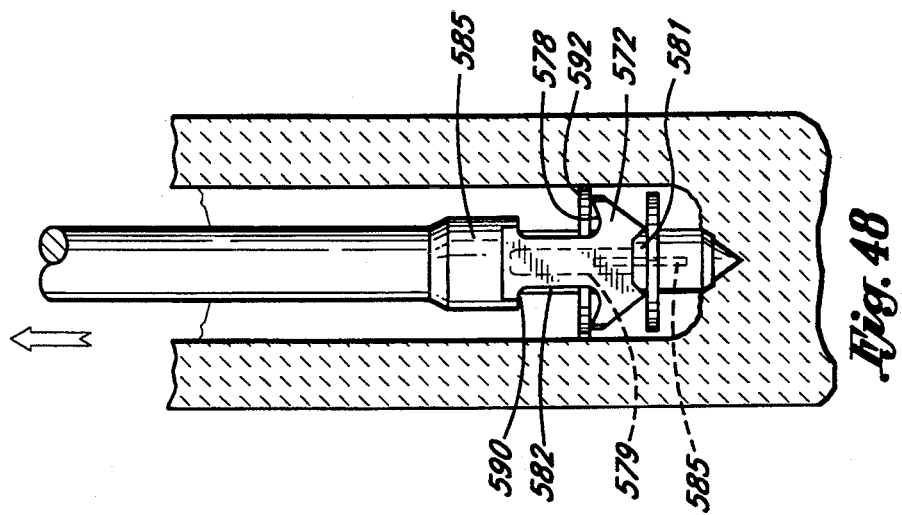
FIG. 48 is a partial cross-sectional view schematically illustrating the poly-plug puller tool bit of FIG. 41 in a position ready to extract the polyethylene plug from the femoral canal.

At its distal end 574, the barbed tip 566 includes an elongated cylindrical shaped aperture 579 extending along the longitudinal axis and opening onto generally concave section 581, as best seen in FIGS. 103 and 106. As shown in FIGS. 42 and 48, the concave section 581 includes a pair of sides 583 which slope in the proximal direction into the aperture 579 to channel a pin 585 of the polyethylene plug 561 into the aperture 579 as the barbed tip 566 passes through the plug 561. The aperture 579 has a sufficient size and length to receive the pin 585 during the removal process.

The transverse width of each projection 572 has sufficient size to define a sufficiently large leverage surface 578 to facilitate the removal of the polyethylene plug 561. The transverse width of the barbed tip 566, however, is preferably as small as possible to facilitate insertion into the narrow distal end of the femoral canal.

The leverage surfaces 578 preferably cant distally with respect to the longitudinal axis of the barbed tip 566 at an angle preferably greater than 5°, and more preferably equal to about 15°. The canted leverage surface 578 functions similar to a hook, biting into the polyethylene plug 561 when retracted.

As shown in FIG. 42, the barbed tip 566 includes a pair of diametrically opposed recesses 580 on the proximal side of the projections 572 to permit the flow of plastic behind the projections 572, thus improving the grip between the leverage surfaces 578 and the polyethylene plug 561. Between the recesses 580, the barbed tip 566 includes a shaft 584 having a cross section commensurate with a cylindrical segment 582 of the polyethylene plug 561. The commensurate fit between the cylindrical segment 582 and shaft 584 stabilizes the barb tip 566 relative to the polyethylene plug 561 which tends to facilitate a clean removal of the plug 561.

On the proximal side of the shaft 584, the barbed tip 566 includes a stop 586 having a cross section larger than the cylinder segment 582. The minimum distance between the leverage surfaces 578 and a distal side 588 of the stop 586 is greater than a distance between a proximal end 590 of the cylindrical segment 582 and the distal side of a plug disk 592, as illustrated in FIG. 48. Consequently, the stop 586 provides the surgeon with a tactile indication of when the projections 572 are positioned on the distal side of the plug disk 592.

Figure 47:
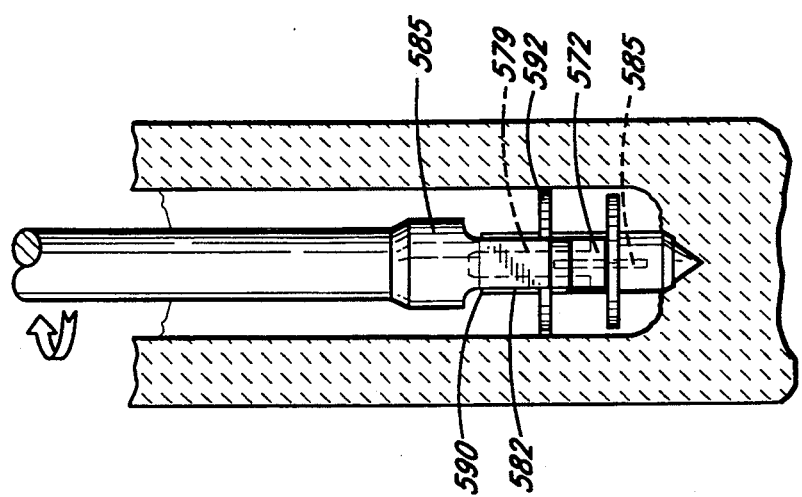
FIG. 47 is a partial cross-sectional view schematically illustrating the insertion of the poly-plug puller tool bit of FIG. 41 into the polyethylene plug.
Figure 46:
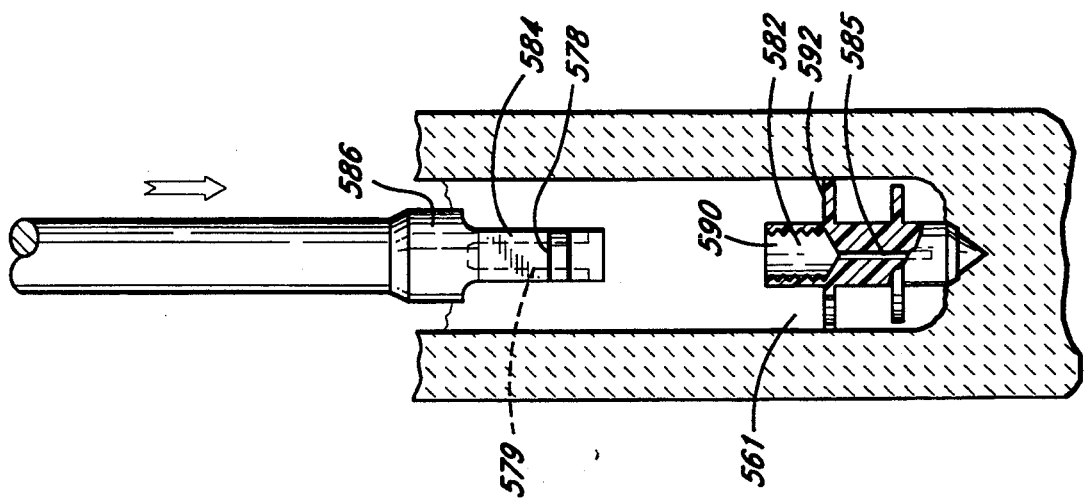
FIG. 46 is a partial cross-sectional view of a distal end of a femoral canal schematically illustrating a partial cross section of a polyethylene plug and a distal end of the poly-plug puller tool bit of FIG. 41.

In use, the ramp surfaces 576 of the barbed tip 566 engage the proximal end 590 of the cylindrical segment of the plug 561. As the surgeon applies a force distally, the projections 572 melt through the cylindrical segment wall 582 with the concave section 581 engaging the pin 585 and channeling it into the aperture 579, as schematically illustrated in FIG. 47. The barbed tip 566 passes through the plug 561 to a point where the stop 586 abuts the proximal end 590 of the cylindrical segment 582, as illustrated in FIG. 47. At this point, the projections 572 are positioned on the distal side of plug disk 592.

The surgeon subsequently rotates the barbed tip 566 through an angle, such as 90°, to position an unmelted portion of the disk 592 on the proximal side of the projections 572. As the barbed tip 566 rotates, plastic may flow into the recesses 580 adjacent to the leverage surfaces 572. The plastic is allowed to cool for about 10 seconds by interrupting the ultrasonic energy before the poly-plug puller 560 is retracted, either manually or with a slide hammer or the like, to remove the plug 561 from the femoral canal.

Each of the foregoing working tips comprises a cross-sectional area through a distal portion thereof which is greater than a cross-sectional area through a more proximal portion thereof to provide a surface for positive interlocking with the cement to be removed. The minimum necessary length of a barb, or increase in cross-sectional area at the distal end of a tool tip, to provide sufficient friction or interfit surface area to withdraw a cement plug from the bottom of the medullary canal can be determined through routine experimentation. In general, however, the scale of the various barbs and lateral projections disclosed herein are in excess of the minimum required to accomplish the plug pulling function of the present invention.

In accordance with the plug-pulling method of the present invention, there is provided a method of removing a deposit of non-biological material from a bone cavity. The method comprises the steps of first identifying a deposit of a non-biological material in a bone cavity. In the preferred application, the present method comprises the removal of a cement plug from the medullary canal as has been previously discussed, during the course of hip revision surgery. Alternatively, the method can be utilized for any of a variety of other surgical procedures in which a non-biological material is desired to be removed from a bone.

In the context of hip revision surgery, the non-biological material typically will comprise a cement for securing a prosthesis to a bone. Frequently, the cement comprises PMMA. Typically, PMMA has a melting point within the range of from about 90° to about 105° C., and a softening point slightly below the melting point as will be readily understood by one of skill in the art. The tool tips and ultrasonic coupling connectors of the present invention are particularly adapted for advancing a tool tip through a PMMA plug by elevating the temperature of the contact area between the ultrasonically activated tool tip and PMMA to a temperature above the softening point of the PMMA.

Thus, in accordance with the present method, at least a portion of the non-biological material is converted from a first hardened state to a second softened state, typically by the application of heat. By "non-biological" material, Applicants intend to define a genus of materials which are softenable as described herein. At the present time, such materials are non-biologicals such as PMMA and other cements. However, cements which may be developed in the future from "biological" materials are also intended to fall within the term non-biological as it is used herein. The removal tool is advanced into the softened portion of the non-biological material, and the softened portion is thereafter permitted to harden around the removal tool. The removal tool is then withdrawn, thereby withdrawing the non-biological material from the bone cavity.

The non-biological material is preferably converted from the first hardened state to the second softened state by the application of ultrasonic energy as has been discussed. Alternatively, the removal tool can be heated through other means, such as by the conduction of an electrical current through the removal tool, or by conducting coherent light (laser light) through a waveguide to the site to be softened.

As a further alternative, a portion of the non-biological material can be converted from a first hardened state to a second softened state by the application of a softening agent, which comprises, in at least one component thereof, a solvent for the non-biological material. Suitable solvents should be suitably biologically compatible for the present application, and can be selected by routine experimentation for any given composition of bone cement.

After a portion of the non-biological material has been softened, the removal tool is advanced into the material to a depth sufficient to provide an adequate friction bond or interference fit to permit the non-biological material to be removed from the bone. For example, referring to the removal tool illustrated in FIGS. 15-20, the tool will be advanced distally into the cement plug until the barb is disposed within the softened cement.

Following implantation of the removal tool into the cement, the tool is preferably rotated about its longitudinal axis to set the barb, and the cement is permitted to harden to provide an interlocking fit with the barb surface of the tool. Sufficient hardening is accomplished by disengaging the ultrasonic energy source, and waiting for the PMMA or other material to cool to a point below its softening point. Typically, this will be accomplished in under about 15 seconds. Alternatively, cooling can be accelerated such as by contacting the cement or tool with a heat sink, or contacting the cement or tool with a coolant such as a circulating fluid or compressed carbon dioxide or other gas, as will be discussed infra.

Following re-solidification of the cement, the removal tool is withdrawn from the bone cavity carrying the cement plug along with it. For this purpose, the removal tool can be provided at its proximal end with appropriate gripping surfaces or an abutment for contacting with a slotted or other removal hammer.

A variety of modifications of the foregoing method and equipment designs can be readily envisioned in view of the disclosure herein. For example, heating may be accomplished by providing a shaped coil outside of the bone and a metal plug puller tip inside, in contact with the PMMA. A 450 kHz inductive welder/brazer energy source could selectively heat the plug puller tip and permit advancement of the tip into the PMMA deposit.

One embodiment of a plug puller tip, including both electrical heating and self-cooling features, is illustrated in FIG. 49. Plug puller tip 600 is provided with a proximal end 601 for coupling to a coolant or electric current source as needed, an elongate body 602 and a pointed distal end 603 for advancing through PMMA cement. Proximal end 601 is provided with means for coupling the tip 600 with a source of electricity in an electrically heated embodiment, and with a source of coolant in a self-cooling embodiment, in a manner well known in the art. For example, Fischer or Lemo type connectors are suitable for the present application.

The distal end 603 of tip 600 is additionally provided with at least one and preferably two or more barbs 604 and 606. Thus, during the removal method, the tip 600 is preferably advanced into the PMMA plug to a sufficient depth that at least distal barbs 604 and 606 are completely imbedded within the cement.

Referring to FIG. 50, there is disclosed an enlarged cross-sectional view of a distal portion of tip 600. Tip 600 in the illustrated embodiment is provided with an inner tubular body 608, disposed concentrically within an outer tubular body 610. Inner tubular body 608 and outer tubular body 610 are connected at a distal point 612. This construction produces a first lumen 614 extending throughout the length of the tip 600 in communication at its distal end with a second lumen 616 also extending throughout the length of the tip 600. A wide variety of alternate designs will be apparent to one of skill in the art in view of the disclosure herein for also providing a first and a second lumen.

The outer tubular body 610 preferably comprises a highly electrically conductive material. Preferably, the outer tubular body 610 comprises a metal having good toughness and corrosion resistance properties such as stainless steel, and an outer plating of copper or silver to enhance conductivity, and a nickel plating over the copper or silver. The inner tube 608 is preferably also highly conductive, and may comprise copper, brass, or copper-plated stainless steel.

In operation, a current is passed between the inner tube 608 and outer tube 610. The distal most region of the tip 600, preferably approximately ⅛ inch, comprises stainless steel without the copper plating. This design creates a relatively high resistance to current flow, and will cause the tip to heat when current is passed between the inner tube 608 and the outer tube 610. In operation, sufficient heat is generated to advance the tip into the PMMA using power levels in the range of from about 2 to about 40 watt, and preferably about 15 watt. Current is thereafter discontinued, and the tip is preferably rotated through an angle such as approximately 90° to set the barbs 604 and 606.

In a self-cooling embodiment, a coolant such as a compressed gas is directed through the first lumen 614 of the inner tube 608. The first lumen 614 is in fluid communication with the second lumen 616 by way of one or more gas ports 618. Thus, compressed gas travelling distally through first lumen 614 travels through port 618 and expands into the relatively low pressure second lumen 616 from which it is vented to atmosphere. Preferably, sterile compressed carbon dioxide is utilized as a coolant.

In this manner, the tip 600 can be rapidly cooled. Although the PMMA solidifies relatively quickly following removal of the heat source, accelerated cooling may be desired in certain applications. In general, any reduction of the overall surgical procedure time is desirable.

The self-heating and cooling tip 600 can be manufactured in any of a variety of ways well known in the art. In addition, plug removal tips having only one of the heating or cooling functions can also be readily produced. For example, an ultrasonically driven tip may also desirably be provided with influent and effluent cooling lumen.

In one embodiment, the elongate body portion 602 comprises a 0.25" diameter, thick wall tubing, which is soldered or glued at its proximal end to the connector shell 601. The elongate body 602 is preferably provided with a stop disk 620 for providing leverage during removal of the tip 600. Stop 620 is preferably securely fastened to the body 602 such as by welding, brazing or swaging.

As illustrated in FIG. 51, which is an end representational view of the stop 620, stop 620 is preferably additionally provided with indicium of rotational orientation. These indicium assist in permitting the clinician to evaluate the degree of rotation of the tip in the softened cement prior to removal. Elongate body 602 is additionally preferably provided with graduated indicium which indicate the depth to which the tip has been advanced into the cement plug. Thus, depending upon the relative dimensions of the tip, including the number of barbs on the distal end thereof, a particular tip will be required to be advanced into the cement plug a distance which corresponds to the dimensions of the barbs.

The tip is preferably constructed by progressive swaging, stamping and/or drawing thick wall tubing, in operations which are readily understood by one of skill in the art. Preferably, the tip tapers to a smaller exterior diameter towards the distal end thereof.

The overall length of the embodiment illustrated in FIG. 49 is approximately 18". The length of the portion of the tip illustrated in FIG. 50 is approximately 0.5". The distance from the distal point of the tip 600 to the transition point 622 is approximately 1.5". The diameter of the tubular body just distally of transition point 622 is approximately 0.15".

In the embodiment in which the proximal portion of body 602 has an outer diameter of 0.25" the outer tubular body 610 has an inside diameter of 0.150. The outside diameter of the inner tube 608 is 0.018 and the inside diameter of the first lumen 614 is 0.010. Outer diameter of 610 in the distal tip region is 0.150, inner diameter of 610 is within the range of from about 0.028–0.050; 0.028 preferred. The volume of the second lumen is greater than the volume of the first lumen, and the second lumen acts as an expansion chamber for compressed coolant. Additional particular dimensions, designs and construction materials will be apparent to one of skill in the art in view of the disclosure contained herein.

The ultrasonic energy conducting extender 46, utilized with ultrasonically heated embodiments, will be understood by reference to FIGS. 5 and 6. The extender 46 enables the tool bit 44 to be spaced apart from the transducer 42 and acoustically couples the tool bit 44 to the transducer handpiece 42, as shown in FIG. 5. The length of the extender 46, like the tool bit 44, is influenced by the operating wavelength and by its intended use.

Preferably, the extender length coincides with the wavelength of the ultrasonic oscillation to position the handpiece/extender junction and the extender/tool junction at antinodes of the oscillation. More preferably, the length of the extender 46 equals 2.022 inches, 4.453 inches or 6.849 inches, plus or minus 20%, preferably plus or minus less than 10%, more preferably plus or minus less than 5% and most preferably plus or minus no more than about 1%.

It is also preferred that the extender 46 includes a stepped diameter with a large fillet 47, as shown in FIG. 6, to amplify the ultrasonic energy, as discussed above in the context of the tool diameter. However, for successive extenders, it is understood that extenders may be provided having a substantially uniform cross-sectional dimension throughout.

Figure 8:
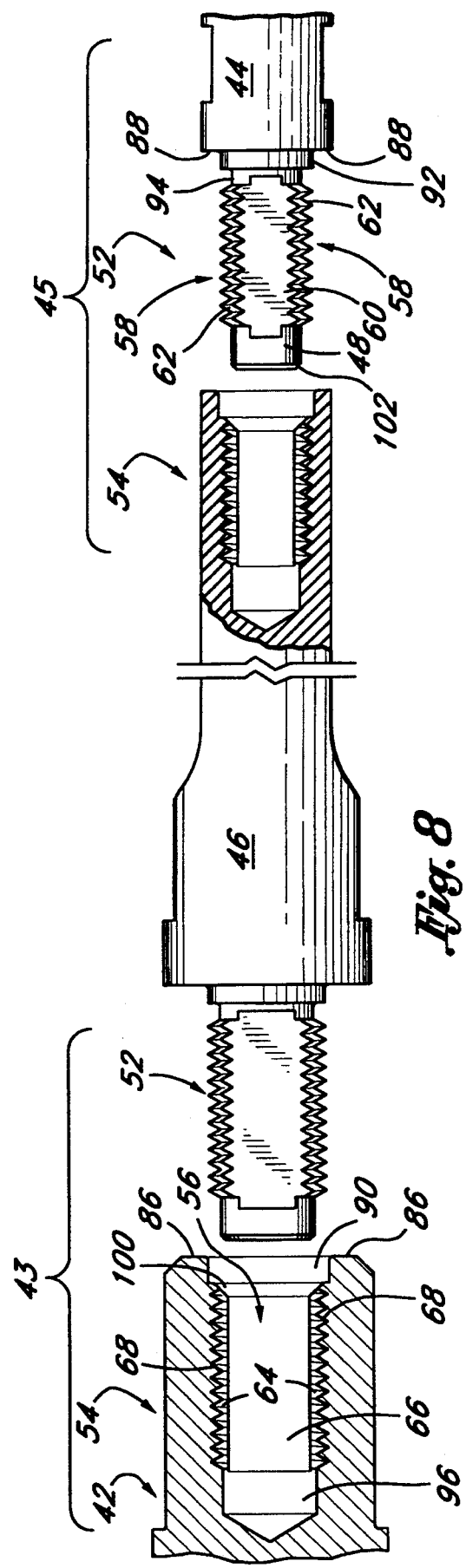
FIG. 8 is an exploded partial cross-sectional view of the junctions of FIG. 7.

Referring to FIG. 8, the tool bit 44 connects to the extender 46 via a second junction 45. Likewise, the extender 46 connects to the handpiece 42 via a first junction 43. It is contemplated that the structure of the first and second junctions 43, 45, apart from diameter, will be substantially identical, and the discussion herein of one will be understood as applying equally to both, unless specified to the contrary.

FIGS. 7-9 illustrate the junctions 43, 45 which comprise a generally cylindrical male component 52 and a tubular female component 54 comprising a generally cylindrical recess 56 adapted to receive the male component 52. These components quickly connect by inserting the male component 52 into the female component 54 and rotating one component with respect to the other component, preferably through a relatively short rotational arc, and optimally about ninety° plus or minus 10°.

When joined, the junction 43 produces a relatively high axial compression force, which is preferably uniformly distributed symmetrically about the contact surfaces between the two components to optimize the transfer of ultrasonic energy across the junction 43. Non uniform distribution of the axial compression force about the longitudinal axis of the junction 43 tends to decrease the efficiency of the transfer of energy across the junction 43, and can cause unwanted transverse motion (whipping) and may lead to premature mechanical failure.

Although FIGS. 6 through 12 illustrate the male component 52 extending in a proximal direction, it is understood that the relationship of the male and female components can be reversed.

Referring to FIGS. 8 and 9, the male component 52 comprises at least two axially extending splines 58 spaced apart by at least two axially extending flats 60. Preferably, the male component 52 comprises two diametrically opposed splines 58 and two diametrically opposed flats 60, alternatively positioned around the circumference of the component, as seen in FIG. 9.

Each spline 58 comprises a plurality of external threads 62 preferably configured in accordance with the American National Standard for Unified Threads ("UN"). It will be understood that other thread configurations, such as the American National Standard Acme Screw Threads ("Acme"), can be used as well. It has been found preferable, however, to employ the UN thread design instead of others, such as the Acme thread design, primarily for manufacturing ease.

Advantageously, the thread pitch and the pitch diameter of the threads 62 and the length of the splines 58 are selected to produce high axial compression between the components without structural failure. It is also preferable to select a generally standard thread for manufacturing convenience. Additionally, the threads must engage to produce high axial compression with little rotation. Preferably, circumferentially, 75% of the threads engage with rotation of no more than about 90° plus or minus 10°. For example, in one preferred embodiment the splines 58 comprise a series of 10-28 UNS-2A threads along a length of 0.315 inches, and in another embodiment, the splines 58 comprises a series of ¼-28 UNF-2A threads along a length of 0.435 inches. In general, the spline preferably comprises about 12 interrupted threads.

In general, the junction 43 has a minimum of 45° of total engagement between the spline threads to produce the high axial compression without mechanical failure. Preferably, the junction has an engagement between about 90°-179° and most preferably about 173° (48% of 360°=172.8°). Thus, in a most preferred embodiment, the sum of the lengths of the threads 62 on the male component measured in a circumferential direction preferably range from 90° to 179°, and more preferably equal 173°.

The circumferential length of each spline thread 58 (i.e., the circumferential width of each spline) depends upon the number of splines 58 employed. For example, in a most preferred embodiment having two splines, the length of the thread 62 in a single spline along the circumferential direction range between 45° and 89.5°, and preferably equal 86.5°.

The female component 54 likewise comprises at least two axially extending splines 64 and at least two axially extending flats 66, disposed on the recess circumference 56 in a corresponding relationship with the flats and splines on the male component, as best seen in FIGS. 7, 12 and 13. Preferably, the female component 54 comprises two diametrically opposed splines 64 and two diametrically opposed flats 66 alternatively positioned around the circumference of the recess 56, as best seen in FIG. 12. Each spline 64 comprises a plurality of internal threads 68 configured to match and engage with the threads 62 on the male component 52.

As discussed above, the sum of the length of the threads 68 around the circumference of the recess 56 is preferably not less than about 90° and not greater than about 179°, and most preferably equal 173°. Each spline thread length depends upon the number of splines employed. For example, in a most preferred embodiment having two splines 64, the threads 68 of each spline 64 extend around the circumference of the recess 56 for at least approximately 45°, but less than approximately 89.5°, and preferably equal 86.5°.

The two splines 64 and two flats 66 alternately disposed on the interior circumference of the female component recess 56 provide an axial key-way 67 for receiving the two opposing splines 58 on the male component 52, as shown in FIG. 12. The male component 52 is inserted into the recess 56 of the female component 54 and rotated to interlock the corresponding splines on the male and female components, as shown in FIG. 13. It is desired that minimum rotation of one component with resect to the other component will produce a junction which achieves a relatively high efficiency of energy transmission therethrough.

In general, it has been found that a high compression across the junction symmetrically distributed about its longitudinal axis optimizes energy propagation. Preferably, the thread 62, 68 design of the junction 50 produces greater than about 300 pounds of axial compression force between the components with rotation of about 90°±10%. More preferably, a compression in excess of about 500 pounds will be achieved. Axial compressions of about 675 lbs. for a junction having an outside diameter of about 0.260 have been measured. Compressions in excess of about 1500 lbs. have been measured with an outside diameter of 7/16 inch, and in excess of about 2300 lbs. have been measured for diameters of 0.750 inches. As a result of higher compression, the ultrasonic pressure wave propagates across the junction with minimal energy loss.

It is preferred that the points of contact between the two joined surgical components be symmetric about the longitudinal axis of the male component 52 to uniformly distribute the compression force about the junction 43 in the radial direction. As a result, the ultrasonic oscillation maintains its propagation along the longitudinal axis of the joined surgical components without deflection from that axis. If deflection occurs, the tool will tend to whip resulting in undesired heat build-up and loss of energy at the tool tip 51.

In this regard, the female component 54 preferably additionally comprises an annular engagement surface 86 on the proximal end thereof which contacts a corresponding annular engagement surface 88 of the male component 52. Preferably, the engagement surface 86 of the female component 54 extends radially outwardly along a plane substantially perpendicular the axis of the internal recess 56, and the engagement surface 88 of the male component 52 extends radially outward along a plane substantially perpendicular to the axis of the male component 52. Referring to FIG. 7, as the splines 58, 64 interlock, the two components draw together to force the engagement surfaces 86, 88 against each other, resulting in an axial compression force across the junction 50.

Preferably, the engagement surfaces 86, 88 are smoothly polished to produce a substantially liquid-tight seal between the components as the surfaces abut. In addition to optimizing energy propagation, a liquid-tight seal reduces cavitation erosion of the components at the junction 50 and thereby extends the life of each component.

In a preferred embodiment, the female component 54 additionally comprises an axially extending, generally cylindrical counterbore 90 at the distal end of the recess 56 for receiving a generally cylindrical shank barrel 92 on the proximal end of the male component 52. The counterbore 90 and the shank barrel 92 are preferably centered with respect to the longitudinal axis of the male component 52. Preferably, the shank barrel 92 smoothly fits into the counterbore 90 to center the female component 54 with respect to the male component 52.

Advantageously, the male component 52 further comprises an undercut region 94 positioned between the engagement surface 88 and the spline 58 so that the spline threads 62 are fully formed (i.e., no run-out region). As a result, the splines 58 can be reduced in overall length, as will be understood in the art.

Referring to FIG. 8, the female component 54 preferably additionally includes a generally cylindrical pilot recess 96 for receiving a corresponding generally cylindrical tip barrel 98 at the proximal end of the male component 52. Preferably, the diameters of the pilot recess 96 and the tip barrel 98 substantially coincide with the minor diameter of the threads 62, 68. Advantageously, the pilot recess 96 and the tip barrel 98 are centered about the longitudinal axis of the male component 52 for optimizing the concentricity of the engagement surfaces 86, 88 between the components to optimize the longitudinal transfer of ultrasonic energy through the junction 43.

To facilitate rapid interconnection between the components, the female component 54 preferably additionally comprises an annular internal chamfer 100 and the male component 52 additionally comprises an annular tip chamfer 102. When the male component 52 is inserted into the female component 54, the chamfers 100, 102 ease the insertion by funneling the components together. Additionally, the edges of the leading spline threads 62 of the male component 52 preferably include a chamfer 104 to ease the engagement between the splines 58, 64 of the male component 52 and female component 54.

Referring to FIGS. 10 through 13, it is preferred that the surgical components include alignment arrows 106 etched on the exterior surface of the components to aid in the connection process. By aligning the arrows, the splines 58 of the male component 52 align with the key-way 67 of the female component 54, as seen in FIGS. 10 and 12. By rotating the components as shown in FIG. 11, the splines 58,64 of the two components interlock, as shown in FIG. 13. Flat opposing surfaces are provided on the exterior surface of all parts to receive a wrench to facilitate tightening and untightening of the junctions.

Those skilled in the art can manufacture the disclosed junction 43 by processes known in the art. For example, the generally cylindrical male component 52 and the shank barrel 92 thereto can be cut into an end of the shank of a surgical component, such as the extender 46 or the tool bit 46. The threads 62 can either be cold rolled onto the cylinder or preferably machine cut into the cylinder. The flats 64 can then be milled onto the component thereby interrupting the threads 62. Finally, the tip barrel 98 can be cut onto the distal end of the male component 52 such as by lathing operations well known in the art and the chamfers 102, 104 similarly added thereto.

The recess 56 of the female component 54 can be made by drilling the pilot hole recess 96 into the end of a surgical component. The counterbore 90 then can be milled and a portion of the pilot hole 96 tapped with the appropriate internal threads by processes known in the art. The flats 66 can be milled and broached into the recess 56 thereby interrupting the threads 68 on the recess 56 wall. Finally, the internal annular chamfer 100 can be drilled or milled to form a smooth transition from the counterbore 90 to the threaded recess 56.

The tool bits and extenders 46 herein can be manufactured from any of a variety of materials known in the art. Preferably, high quality factor materials are used due to their known superiority in propagating ultrasonic energy. More preferably, a 400 series stainless steel or titanium is used because of their relative biocompatibility and their strength. Most preferably, a high grade titanium, such as Ti-6A1-4V alloy (aircraft grade 5), AA sonic inspected, is used.

An ultrasonic technique may also be employed for implanting an original or a replacement prosthesis during revision surgery. The preparation of a cavity in which a prosthesis is placed can be tedious and careful shaping of the cavity is important so that a tight fit is obtained. This is particularly significant for implantation of prostheses having porous surfaces for ingrowth of cancellous bone. At present such a cavity is formed by drilling and reaming to form a cavity of roughly the right shape and size and then finishing the cavity with a rasp or series of rasps complementary to the shape of the prosthesis, which are hammered or pressed into the medullary canal.

In practice of this invention at least the final reaming of the cavity is done by ultrasonically vibrating an object having the same shape as the prosthesis, with sufficient energy to disrupt cancellous bone, and pressing the ultrasonically vibrating object into the cancellous bone for forming a cavity complementary to the prosthesis. Preferably the object has rasp-like teeth which further aid in disrupting cancellous bone so that the object can be pressed into the cavity without excessive force which could fracture the cortex.

The object employed for forming a cavity in the cancellous bone complementary to the prosthesis may be a rasp that is inserted and temporarily left in place for testing and other procedures before the prosthesis is implanted. Preferably the object comprises the prosthesis itself. Thus, as illustrated in FIG. 4, a prosthesis 36 such as the femoral component of a hip joint has a plurality of rasp-like teeth on surface areas 37 on at least the tapering body portion of the prosthesis. An exemplary size for the rasp-like teeth is about 400 micrometers peak-to-peak. An ultrasonic transducer 38 is coupled to the self-holding taper 39 on the neck of the prosthesis as hereinabove described. As the prosthesis is ultrasonically vibrated by the transducer, it is pressed into the cavity and the teeth cut cancellous bone until the prosthesis fits tightly in the cavity. The transducer can then be removed and the prosthesis left in the cavity so formed.

It is not important that the scarf produced by the teeth on the prosthesis be removed from the cavity. On the contrary, it is not unusual to pack a portion of the cavity with fragments of cancellous bone and tissue removed in forming the cavity to assure a tight fit of the prosthesis. Such materials appear to promote growth of cancellous bone and may enhance fixation of a porous ingrowth prosthesis in the cavity. It is desirable to employ teeth with a spacing from about 50 to 400 micrometers since that is appropriate for ingrowth of cancellous bone. Thus, the newly grown cancellous bone between the teeth tends to secure the prosthesis in the cavity. In other words, the teeth are analogous to the porous surface on conventional ingrowth type prostheses.

Although limited embodiments have been described and illustrated herein, it will be readily appreciated by those skilled in the art that there may be many modifications and variations of practice of this invention. For example, although coupling the ultrasonic transducer to the self-holding taper on a prosthesis is particularly desirable, any of a variety of coupling means may be employed. As should already be apparent from the description, these techniques may be employed in combination with other conventional techniques for loosening and removing a prosthesis from a joint.

Further, although described in the context of a hip joint replacement, it will be apparent that similar techniques may be used with implants of shoulder joints, knees and the like, or with pins used for reinforcing bone. For example, ultrasonic vibrations may be used for implanting the keel of the tibial component of a knee joint. Ultrasonic vibration of a rasping object may be used for final shaping of the cavity for an acetabular cup. It is, therefore, to be understood that within the scope of the appended claims, this invention may be practiced otherwise then as specifically described.

It is claimed:

1. A method of removing a deposit of cement from a cavity in a bone, comprising the steps of:
    identifying a deposit of a cement in a bone cavity;
    providing a removal tool comprising a working tip;
    transmitting coherent light through a fiber optic waveguide to said working tip of said removal tool;
    converting the energy of the coherent light to thermal energy at the working tip of the removal tool to heat at least a portion of the working tip;
    conducting heat from said removal tool to the cement;
    converting at least a portion of the cement from a first hardened state to a second softened state;
    advancing the working tip of the removal tool into the softened portion of the cement;
    permitting the softened portion of the cement to return to the first hardened state; and thereafter
    withdrawing the removal tool, thereby withdrawing the cement from the bone cavity.

2. A method as in claim 1, wherein the cement comprises polymethylmethacrylate.

3. A method as in claim 1, additionally comprising the step of deactivating the transmission of coherent light.

4. A method as in claim 1, additionally comprising the step of conducting heat away from the cement and the working tip of the tool, to permit the cement to harden around the working tip.

5. A method as in claim 4, wherein said step of conducting comprises contacting the cement with a heat sink.

6. A method as in claim 5, wherein said step of conducting comprises contacting the cement with a coolant.

7. A method as in claim 6, wherein said coolant comprises carbon dioxide.

8. A method as in claim 4, wherein said step of conducting heat away from the cement comprises the step of flowing a coolant medium through an interior passage which extends through said working tip.

9. A method as in claim 8, wherein said coolant comprises carbon dioxide.

10. A method as in claim 1, wherein the cross-sectional area through at least a portion of the working tip is greater than the cross-sectional area through at least a portion of the removal tool on the proximal side of the working tip, and wherein the method additionally comprises the step of rotating said tool to position the working tip beneath a portion of the cement remaining in the first hardened state to interlock the tool with the deposit of cement.

11. A method as in claim 1, wherein said working tip has at least one barb and the method additionally comprises the step of rotating said removal tool to position the barb beneath a portion of the cement remaining in the first hardened state to interlock the tool with the deposit of cement.

* * * * *